US010287618B2

(12) United States Patent
Ahimou et al.

(10) Patent No.: US 10,287,618 B2
(45) Date of Patent: May 14, 2019

(54) WASH MONITOR COMPOSITION, DEVICE, AND METHOD OF USE

(71) Applicant: 3M INNOVATIVE PROPERTIES COMPANY, St. Paul, MN (US)

(72) Inventors: Francois Ahimou, Woodbury, MN (US); RuthAnn R. Duda, Eagan, MN (US); G. Marco Bommarito, Stillwater, MN (US); Timothy J. Nies, Stillwater, MN (US); Kai Qiu, Shangahi (CN)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 39 days.

(21) Appl. No.: 15/129,442

(22) PCT Filed: Mar. 24, 2015

(86) PCT No.: PCT/US2015/022110
§ 371 (c)(1),
(2) Date: Sep. 27, 2016

(87) PCT Pub. No.: WO2015/148427
PCT Pub. Date: Oct. 1, 2015

(65) Prior Publication Data
US 2017/0175163 A1 Jun. 22, 2017

Related U.S. Application Data

(60) Provisional application No. 61/971,933, filed on Mar. 28, 2014.

(51) Int. Cl.
*C12Q 1/22* (2006.01)
*A61L 2/28* (2006.01)
(Continued)

(52) U.S. Cl.
CPC ............... *C12Q 1/22* (2013.01); *A61B 90/70* (2016.02); *A61L 2/04* (2013.01); *A61L 2/18* (2013.01);
(Continued)

(58) Field of Classification Search
CPC ............. C12Q 1/22; A61L 2/18; A61B 90/70
See application file for complete search history.

(56) References Cited

U.S. PATENT DOCUMENTS

| 4,978,504 A | 12/1990 | Nason |
| 5,266,266 A | 11/1993 | Nason |

(Continued)

FOREIGN PATENT DOCUMENTS

| DE | 44 37 103 | 4/1996 |
| EP | 1 769 808 | 4/2007 |

(Continued)

OTHER PUBLICATIONS

Amin, S.R. et al.; "Assessing the Effectiveness of Surface Cleaning Methods in Intravitreal Injection Procedure Rooms"; American Academy of Ophthalmology; vol. 121, No. 1; 2014; pp. 276-282 (XP055194821).

(Continued)

*Primary Examiner* — Narayan K Bhat
(74) *Attorney, Agent, or Firm* — 3M Innovative Properties Company; Trisha D. Adamson

(57) ABSTRACT

A composition for monitoring the efficacy of a decontamination process is provided, the composition comprising a cellulose polymer and a predetermined quantity of an adenine nucleotide. A monitoring device comprising a test element with the composition disposed thereon is also provided. The composition and/or monitoring device can be used in a method. The method includes exposing the monitoring device to a decontamination process and subsequently (Continued)

measuring the residual tracer analyte on the monitoring device.

11 Claims, 10 Drawing Sheets

(51) Int. Cl.
*A61L 2/04* (2006.01)
*A61B 90/70* (2016.01)
*A61L 2/18* (2006.01)

(52) U.S. Cl.
CPC ........... *A61L 2/28* (2013.01); *A61B 2090/702* (2016.02); *A61L 2202/17* (2013.01); *A61L 2202/24* (2013.01)

(56) References Cited

U.S. PATENT DOCUMENTS

| | | | | |
|---|---|---|---|---|
| 5,756,049 | A * | 5/1998 | Brayton | B01L 3/50825 422/430 |
| 5,879,635 | A | 3/1999 | Nason | |
| 6,130,054 | A * | 10/2000 | Iwata | C12Q 1/48 435/14 |
| 7,485,262 | B2 * | 2/2009 | DiCesare | B01L 3/5029 422/404 |
| 7,618,591 | B2 * | 11/2009 | Slowey | A61B 10/02 422/412 |
| 2003/0012688 | A1 | 1/2003 | Kippenhan, Jr. | |
| 2003/0164182 | A1 | 9/2003 | Jacobs et al. | |
| 2005/0208295 | A1 * | 9/2005 | Saika | C12Q 1/06 428/343 |
| 2012/0100531 | A1 * | 4/2012 | Rajagopal | B01L 3/5029 435/6.1 |
| 2012/0149006 | A1 | 6/2012 | Padilla De Jesus et al. | |

FOREIGN PATENT DOCUMENTS

| | | |
|---|---|---|
| WO | WO 1993/00994 | 1/1993 |
| WO | WO 2009/134509 | 11/2009 |
| WO | WO 2014/058652 | 4/2014 |
| WO | WO 2014/133854 | 9/2014 |

OTHER PUBLICATIONS

Amodio, E. et al.; Use of ATP bioluminescence for assessing the cleanliness of hospital surfaces: A review of the published literature (1990-2012); Journal of Infection and Public Health; 2013; pp. 1-7.

Masuku, S.M. et al.; "Cleaning and decontamination efficacy of wiping cloths and silver dihydrogen citrate on food contact surfaces"; Journal of Applied Microbiology; vol. 113; 2012; pp. 89-95.

Moore, G. et al.; "The use of adenosine triphosphate bioluminescence to assess the efficacy of a modified cleaning program implemented within an intensive care setting"; American Journal of Infection Control; vol. 38 No. 8; 2010; pp. 617-622 (XP027275557).

\* cited by examiner

WASH MONITOR COMPOSITION, DEVICE, AND METHOD OF USE

CROSS REFERENCE TO RELATED APPLICATIONS

This application is a national stage filing under 35 U.S.C. 371 of PCT/US2015/022110, filed Mar. 24, 2015, which claims priority to U.S. Provisional Patent Application No. 61/971,933, filed Mar. 28, 2014, the disclosure of which is incorporated by reference in its entirety herein.

BACKGROUND

Hospitals and clinics frequently rely on washing equipment and processes to remove biological soil from reusable medical instruments and devices (i.e., to decontaminate the instruments and devices). In addition, the solvent used in the decontamination processes may contain chemical and/or enzymes to facilitate the removal and/or disinfection of the biological soil. In operation, the washing equipment can fail to adequately clean the instruments and devices due to one or more of a variety of reasons including, for example, washing the objects at an unacceptably low temperature and providing an inadequate volume and/or velocity of solvent to the washing process. In addition, the wash solvent can fail to adequately clean the instruments and devices due to one or more of a variety of reasons including, for example, loss of chemical and/or enzyme activity due to aging and improper dilution of active ingredients (e.g., chemicals or enzymes) in the wash solvent.

Disposable wash monitors are used for monitoring the efficacy of wash processes in washer-disinfector equipment, for example. A wash monitor typically includes a test soil disposed on a surface of an object that is placed into a washing machine. The test soil may comprise biological molecules such as, for example, human or animal red blood cells, protein, and fat. The monitor also includes a detectable marker (e.g., a pigment or dye) that can be observed to determine whether the washing machine meets minimum requirements for impinging a wash solution against an object and/or to determine whether the wash solution meets minimum requirements for chemical and/or enzymatic treatment of the object to be cleaned.

Although a variety of wash monitors are available to assess the efficacy of a decontamination process, there remains a need for improved decontamination monitors.

SUMMARY

The present disclosure generally relates to a dried composition, a monitoring device, and a method to assess the efficacy of a decontamination process and a method of use thereof. In particular, the present disclosure provides a monitoring device with a test element having the dried composition disposed thereon. The composition comprises a cellulose polymer, a predefined quantity of a tracer analyte and, optionally, a sugar. In use, the test element is exposed to a decontamination process wherein, if the decontamination process is efficacious for decontaminating objects with biological soil disposed thereon, the tracer analyte is substantially removed from the test element. Advantageously, the tracer element can be quantified in the monitoring device using a corresponding analytical instrument.

In any embodiment, the monitoring device of the present disclosure comprises a test portion that has at least one cavity in which the dried composition is disposed. Advantageously, the at least one cavity poses a barrier to removal of the dried composition from the test portion. Accordingly, the monitoring device can be used to distinguish between at least two distinct failure modes that are related to sub-processes (e.g., wash step and rinse step) of an automated decontamination process.

In one aspect, the present disclosure provides a method of assessing the efficacy of a decontamination process. The method can comprise exposing a test portion of a monitoring device to a decontamination process. The test portion includes a dried composition removably adhered thereto. The dried composition can comprise a cellulose polymer and a predetermined first quantity of an adenine nucleotide. After exposing the test portion to the decontamination process, the method further can comprise contacting the test portion with a detection reagent for detecting the adenine nucleotide, using the detection reagent to measure a second quantity of the adenine nucleotide remaining on the test portion; and comparing the second quantity to a predetermined first threshold quantity. In any embodiment, comparing the second quantity to a predetermined threshold quantity further can comprise comparing the second quantity to a plurality of predetermined threshold quantities. In any of the above embodiments, the method further can comprise the steps of comparing the second quantity of the adenine nucleotide to a second threshold quantity and reporting an outcome of an assessment of the efficacy wherein, when the second quantity is less than or equal to the first threshold quantity, the outcome of the decontamination process is reported to indicate the process was efficacious and wherein, when the second quantity is greater than the first threshold quantity but less than or equal to a second threshold quantity, the outcome of the decontamination process is reported to indicate the process had a deficiency associated with a first predetermined parameter of the decontamination process.

In another aspect, the present disclosure provides a method of processing an object to be decontaminated. The method can comprise processing, in one load in a decontamination process, an object having an unknown amount of biological soil disposed thereon and/or therein and a monitoring device comprising a test portion. The test portion includes a dried composition removably adhered thereto. The dried composition can comprise a cellulose polymer and a predetermined first quantity of an adenine nucleotide. After processing the batch in the decontamination process, the method further can comprise contacting the test portion with a reagent for detecting the adenine nucleotide, using the detection reagent to measure a second quantity of the adenine nucleotide remaining on the test portion, and comparing the second quantity to a predetermined first threshold quantity.

In yet another aspect, the present disclosure provides a monitoring device. The monitoring device can comprise a container comprising a first end with an opening dimensioned to receive a test element; a test element disposed in the container, the test element comprising a test portion; a dried composition releasably adhered to the test portion, the dried composition comprising a cellulose polymer and a predetermined quantity of an adenine nucleotide; and a reagent for detecting the adenine nucleotide, the reagent disposed in the container. In any embodiment, a kit can comprise the monitoring device.

In yet another aspect, the present disclosure provides an article. The article can comprise a dried composition removably adhered thereto. The dried composition can comprise a cellulose polymer and a predetermined amount of an adenine nucleotide.

In yet another aspect, the present disclosure provides a system. The system can comprise a monitoring device, an analytical instrument, and a processor configured to receive electronic data from the analytical instrument and to process or report the data. The monitoring device can comprise a test element disposed in the container, the test element comprising a test portion; a dried composition releasably adhered to the test portion; and a reagent for detecting an adenine nucleotide, the reagent disposed in the container. The dried composition can comprise a cellulose polymer and a predetermined quantity of an adenine nucleotide. The analytical instrument can be an analytical instrument for detecting a reaction between the adenine nucleotide and the reagent.

In any of the above embodiments, the dried composition can comprise a sugar. In any of the above embodiments, the cellulose polymer can comprise a water-soluble cellulose polymer.

"Decontaminate" and "decontamination process", as used herein refers to processes that use an aqueous medium for the removal of adherent contamination from surfaces. The adherent "contamination" includes, but is not limited to, microbial contamination, bacterial contamination, proteinaceous contamination, residual contamination, and gross contamination.

"Disinfection", as used herein, refers to a reduction of the number of viable microorganisms on a surface to a level previously specified as appropriate for its intended further handling or use.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, "a," "an," "the," "at least one," and "one or more" are used interchangeably. Thus, for example, a test portion comprising "a" cavity can be interpreted to mean that the test portion can comprise "one or more" cavities.

The term "and/or" means one or all of the listed elements or a combination of any two or more of the listed elements.

Also herein, the recitations of numerical ranges by endpoints include all numbers subsumed within that range (e.g., 1 to 5 includes 1, 1.5, 2, 2.75, 3, 3.80, 4, 5, etc.).

The features and advantages of the present invention will be understood upon consideration of the detailed description of the preferred embodiment as well as the appended claims. These and other features and advantages of the invention may be described below in connection with various illustrative embodiments of the invention.

The above summary of the present invention is not intended to describe each disclosed embodiment or every implementation of the present invention. The figures and the detailed description which follow more particularly exemplify illustrative embodiments. Other features, objects and advantages will become apparent from the description and drawings, and from the claims.

DETAILED DESCRIPTION

Figure 1:
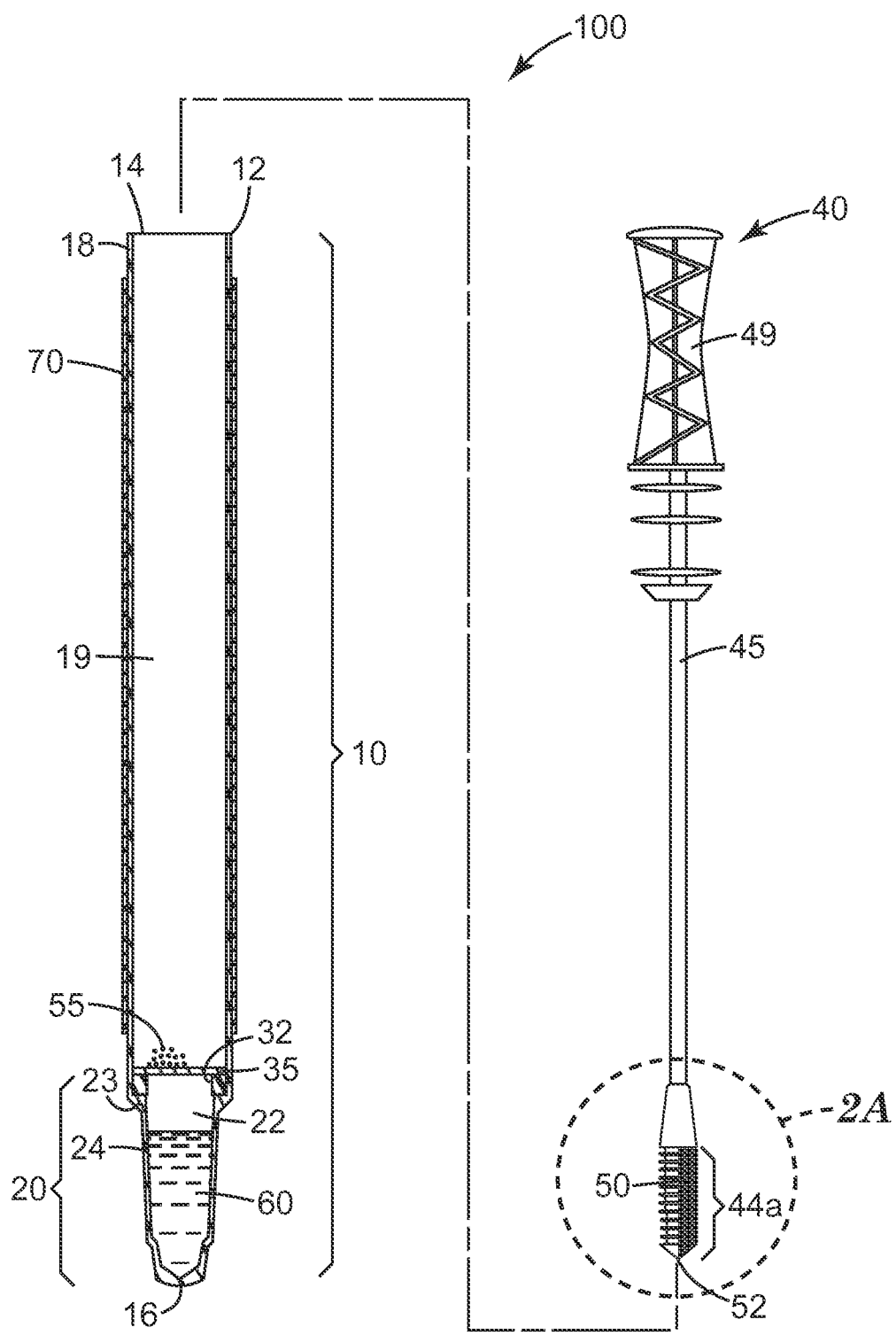
FIG. 1 is a partially-exploded view of one embodiment of a device comprising a unitary container, shown in cross-section, and a test element according to the present disclosure.

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "connected" and "coupled" and variations thereof are used broadly and encompass both direct and indirect connections and couplings. Further, "connected" and "coupled" are not restricted to physical or mechanical connections or couplings. It is to be understood that other embodiments may be utilized and structural or logical changes may be made without departing from the scope of the present disclosure. Furthermore, terms such as "front,"

"rear," "top," "bottom," and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

The present disclosure relates to a process monitor and a method of use thereof. The process monitor device of the present disclosure can be used to test the efficacy of a decontamination process and, in particular, a decontamination process conducted by automated equipment (e.g., an automated washer). The device is an adaptation of existing test devices that are currently used to detect the presence or quantity of a chemical analyte. The existing devices comprise a sample acquisition element (e.g., a swab or dipstick) that is configured for contact with a liquid or solid sample such that the sample acquisition element retains at least a portion of the sample. The sample acquisition element is subsequently inserted into a container where it contacts a detection reagent that reacts directly or indirectly with the analyte to form a detectable product (i.e., a colored compound) that can be observed, and optionally quantitated, by visible inspection or by using an analytical instrument (e.g., a spectrophotometer or luminometer).

The inventive process monitor includes a test element, which is analogous to the sample acquisition element described above, but has been modified in a way that renders it substantially unsuitable for its original purpose (i.e., to detect unknown quantities of analyte). The modification includes deliberately adulterating the test element with a predetermined quantity of tracer analyte that the existing test device was designed to detect. Furthermore, tracer analyte is applied to the test element in such a way that a portion or all of the tracer analyte is released from the test element when the test element is exposed to a decontamination process that meets or exceeds predefined standards for efficacy.

Typically, the test devices include a sample-acquisition element to obtain a sample to be tested and a container into which the sample acquisition element and/or sample can be placed in order to detect the analyte. The container may include a detection reagent disposed therein, the detection reagent capable of interacting with the analyte to form a detectable moiety (e.g., a chemical derivative of the analyte or a detectable byproduct of the interaction such as light, for example). In addition, many of the test devices are adapted to be used with an analytical instrument to obtain the result of the test. For example, the container of the test device may be shaped and dimensioned so that at least a portion of the container can be inserted into the analytical instrument and the test result (e.g., the quantity of analyte detected on the sample acquisition element) is automatically read, and optionally exported and/or electronically saved, by the instrument.

In any embodiment, the tracer analyte is an adenine nucleotide (e.g., adenine-5'-monophosphate (AMP), adenine-5'-diphosphate (ADP), adenine-5'-triphosphate (ATP)). A particularly preferred tracer analyte is adenosine-5'-triphosphate. ATP is readily detected via an enzyme-catalyzed bioluminescent reaction and can be detected using an instrument that can distinguish amounts of ATP over approximately a 6-log range. Nonlimiting examples of existing test devices for ATP include the 3M CLEAN-TRACE Surface ATP Swab available from 3M Company (St. Paul, Minn.), the AQUASNAP ATP Water Test available from Hygiena (Camarillo, Calif.), and the ACCUPOINT 2 ATP Sanitation Monitoring System available from Neogen Corporation (Lansing, Mich.).

A person having ordinary skill in the art will recognize that AMP and ADP can be converted readily to ATP using enzyme-catalyzed reactions known in the art. Thus, using a coupled enzyme assay, it is possible to measure residual AMP or ADP on a test element by converting the AMP or ADP to ATP, which can be measured subsequently via a bioluminescent reaction.

The inventive devices of the present disclosure embody at least one modification of these test devices. The devices are modified such that the sample acquisition element of the original test device (hereinafter, called the "test element" of the modified device) is adulterated with a dried composition that comprises a predetermined quantity of the tracer analyte the test device is designed to detect. In any embodiment, the dried composition can be substantially homogeneous. In contrast to a typical prior art test device, which is configured to detect the absence, presence, or quantity of a particular analyte; the modified test device is configured to detect whether the test element has been exposed to an environment that diminished or eliminated the tracer analyte-containing dried composition imbued thereon.

In one aspect, the present disclosure provides a monitoring device. The device can be used in a variety of methods disclosed herein. FIG. 1 shows an exploded view of one embodiment of a device 100 according to the present disclosure. The device 100 comprises a container 10 and a test element 40. The test element 40 comprises a test portion 44a, to which a dried composition 50 is releasably adhered, and a handle 49. In any embodiment, the container 10 comprises a sleeve 18 coupled to a cuvette chamber 22. The container 10 has a first end 12 and a second end 16 opposite the first end. The first end 12 of container 10 comprises opening 14 into which at least a portion of a test element 40 can be inserted.

The container 10 can be formed (e.g., by injection molding or extrusion) of polymeric materials (e.g., polyethylene, polypropylene) as a unitary part. As with the existing test devices described herein, when detection of the tracer analyte comprises optical detection of a product (e.g., a colored reaction product or a detectable wavelength of light emission) derived therefrom, the container 10 should be formed using materials and processes that permit the transmission of wavelengths of light that are suitable to permit optical detection of the product.

Optionally, the device 100 further may comprise a frangible seal 35 disposed in the container 10. The frangible seal 35, if present can partition the container 10 into two chambers, a receiving chamber 19 proximate the opening 14 and a cuvette chamber 22 distal the opening 14. The frangible seal 35 can be made from a water-resistant material such as, for example, a plastic film, a metal foil, or a metal-coated plastic film. The frangible seal 35 can be coupled to the container 10 via coupling means that are known in the art (e.g., an adhesive, an ultrasonic weld, and the like). The frangible seal 35 may be directly coupled (not shown) to the container 10 at a structure such as flange 23, for example. Alternatively, the frangible seal 35 can be coupled (e.g., via an adhesive, an ultrasonic weld, or the like) to a separate structure (e.g., sealing member 32), which can be inserted into the container 10 and disposed against flange 23, as shown in FIG. 1. The sealing member 32 can be formed from a relatively flexible and/or malleable material such as, for example, polyethylene, polypropylene, silicone, or butyl rubber. Preferably, the frangible seal 35 and sealing member 32, if present, form a liquid-resistant barrier between the receiving chamber 19 and the cuvette chamber 22.

The container 10 can be formed (e.g., by injection molding or extrusion) of polymeric materials (e.g., polyethylene, polypropylene, polystyrene, polycarbonate). The walls of the cuvette portion 20 can be molded, for example, to form one of a variety of geometric shapes such as, for example, cubic, cuboid, cylindrical, conical, frusto-conical, other geometric shapes suitable to be operationally coupled to an analytical instrument (not shown). Preferably, the wall 24 of the cuvette portion 20 can be configured (e.g., by using a relatively transparent or translucent material and/or by constructing the cuvette portion with at least one relatively thin wall 24) to permit the transmission of light (e.g., visible light) into and/or out of the cuvette portion.

An optional lamina 70 can be affixed (e.g., adhesively affixed) to the container (e.g., proximate the opening). The lamina 70 can be made from paper or a plastic film, for example, and may be used as a label.

The device further comprises a detection reagent 55 disposed in the container. In the illustrated embodiment, the detection reagent 55 is disposed in the container as a solid (e.g., a solid powder). In any embodiment, the detection reagent may be dissolved or suspended in a solvent as described below. In some embodiments (not shown), the device may comprise a second frangible seal disposed between the first frangible seal and the opening. The space between the first and second frangible seals forms a compartment in which the reagent, either in dry (e.g., powder) or liquid form, can be disposed.

Optionally, in any embodiment, the container can include a solvent disposed therein. In the illustrated embodiment, the first solvent 60 is disposed in the cuvette chamber 22. In any embodiment (not shown), the solvent alternatively or additionally may be disposed in the receiving chamber 19. In any embodiment, the frangible seal 35 can prevent unintended movement of the first solvent 60 between the receiving chamber 19 and the cuvette chamber 22.

In any embodiment, the first solvent 60 can be a liquid in which a portion (e.g., the tracer analyte) or all of the dried composition 50 is soluble. In any embodiment, the first solvent 60 may comprise water. In some embodiments, the first solvent 60 additionally comprises a buffer component to maintain the solvent within a predefined pH range (e.g., a pH range that is suitable for a reaction used in the detection of the tracer analyte). In some embodiments, the solvent may comprise a surfactant (e.g., a nonionic surfactant) to facilitate the dispersion of the tracer analyte and/or dried composition 50 into the first solvent 60. A suitable surfactant does not substantially interfere with a reaction, a detection reagent, and/or instrument that is used for the detection of the tracer analyte.

A device of the present disclosure comprises a detection reagent for detecting the tracer analyte. In some embodiments, the device may comprise a plurality of detection reagents. At least one detection reagent may be disposed in the container. In any embodiment, at least one detection reagent may be disposed in a sealed chamber (e.g., the cuvette chamber) of the container. In any embodiment, the at least one detection reagent may be dissolved in the solvent. In some embodiments, (not shown) the detection reagent may be disposed on (e.g., as a coating such as a dried coating) and/or in the test element (e.g., dissolved in a solvent disposed in a reservoir, as disclosed herein). The particular detection reagent disposed in the device is selected according to the tracer analyte and/or the instrument that is used to detect the tracer analyte, the derivative of the tracer analyte, or the byproduct of the tracer analyte. A person having ordinary skill in the art will recognize a suitable detection reagent for a particular tracer analyte.

By way of example, suitable detection reagents to detect a protein tracer analyte include a $Cu^{2+}$ compound (e.g., $CuSO_4$), sodium tartrate, sodium carbonate, sodium bicarbonate, and bicinchoninic acid. One or more of the foregoing reagents can be provided in a container according to the present disclosure. By way of another example, suitable detection reagents to detect ATP tracer analyte include luciferin and luciferase. In any embodiment, a first detection reagent may be provided in one part of the container (e.g., the receiving chamber) and a second detection reagent may be provided in another part of the container (e.g., the cuvette portion.

In some embodiments, the solvent may comprise a stabilizer (e.g. an enzyme activity stabilizer).

Referring back to FIG. 1, the test element 40 comprises a test portion 44a and an optional stem 45. The stem 45 can be constructed from a variety of materials, such as wood, plastic, metal, or combinations thereof. In some embodiments, the stem 45 can be fabricated from a sufficiently flexible material (e.g., metal wire or plastic polymer) to insert the test portion 44a into tortuous spaces. Advantageously, in those embodiments, the test element can be used to assess the ability of a washing process to penetrate effectively into the tortuous spaces. In other embodiments, the stem 45 can be relatively inflexible. The stem 45 is adapted to be coupled (e.g., by friction fit or via an adhesive) to the handle 49. In use, the stem 45 or the handle 49 can be grasped by an operator in order to avoid contact between the operator and the test portion 44a and or dried composition 50.

Figure 6:
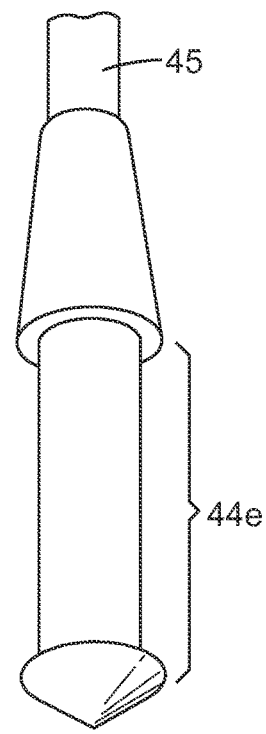
FIG. 6 is a perspective view of another alternative embodiment of a test portion according to the present disclosure.

In any embodiment, the test portion can be a substantially smooth surface such as, for example, test portion 44e of FIG. 6. Alternatively, the test portion may include additional (e.g., 3-dimensional) structural features. The additional structural features provide a greater challenge to a decontamination process because the structural features provide physical obstacles that hinder the removal of the dried composition 50 from the test portion. In any embodiment, the dried composition 50 can be applied as a liquid mixture and/or liquid suspension to the test portion 44a using processes that are known in the art including, for example, kiss coating, dip coating and spray coating. A portion or all of the liquid can subsequently be removed from the composition by evaporation (e.g., by placing the test element into a biosafety hood at ambient temperature (e.g., about 23° C.) for about 2-3 hours, for example). In the illustrated embodiment of FIG. 1, the test portion 44a is shown in partial section in order to show the dried composition 50 coated on one side of the test portion and the underlying structure (e.g., stem 45) on the other side of the test portion. In any embodiment, the dried composition 50 may be coated on the entire circumference of the test portion 44a.

Figure 2A:
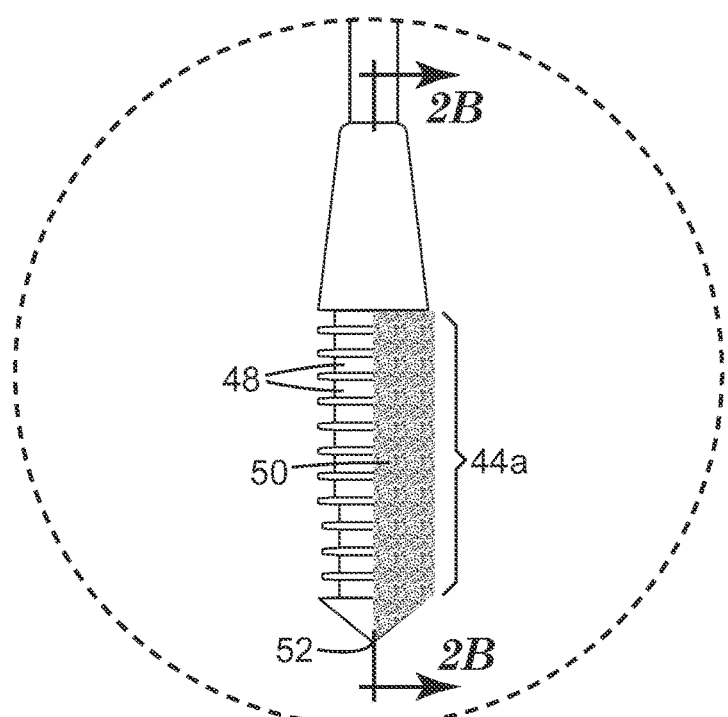
FIG. 2A is a detail side view, partially in section, of the test portion of the test element of FIG. 1.
Figure 2B:
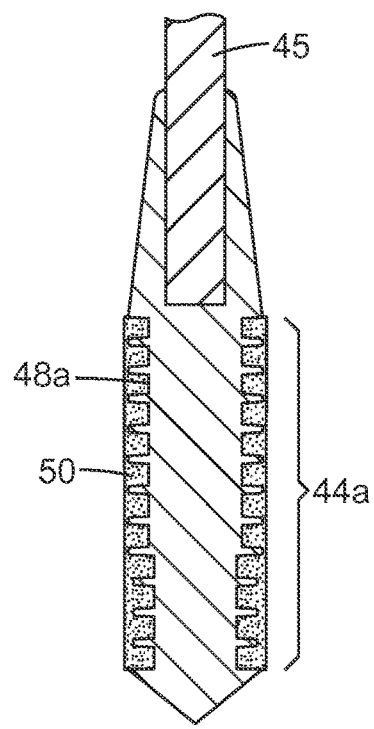
FIG. 2B is a cross-sectional side view of the test portion of FIG. 2A.

FIGS. 2A-2B show detail views of the test portion 44a of the test element 40 of FIG. 1. In this embodiment, the test portion 44a comprises 3-dimensional features. The test portion 44a in this embodiment comprises one or more cavity 48a. In this embodiment, the cavities 48a are illustrated as grooves that encircle the test portion 44a. Although they are illustrated as being substantially uniform in depth and width, it is contemplated that individual cavities may vary in size.

In any embodiment, the stem 45 and test portion 44a may be formed as a unitary part or may be formed as separate parts that are coupled together (e.g., by friction fit or via an adhesive). The test portion 44a may be formed at least in part of relatively rigid polymer (e.g., nylon, polysulfone, polycarbonate, or combinations thereof) or it may be formed using a more compliant polymer, such as silicone. Suitable materials for test portion 44a include, but are not limited to, any thermoplastic materials suitable for casting, profile extrusion, molding (e.g., injection molding) or embossing including, for example, polyolefins, polyesters, polyamides, poly(vinyl chloride), polymethyl methacrylate, polycarbonate, nylon, and the like. In other embodiments, test portion 44a may be formed by molding or embossing a sheet of suitable material into the desired cavity structure. In any embodiment, the test portion 44a may be treated (e.g., corona-treated or electron beam-treated) in order to make the surface of the material more hydrophilic. In the illustrated embodiment of FIG. 2A, the test portion 44a is shown in partial section in order to show the dried composition 50 coated on one side of the test portion and the underlying structure (e.g., cavities 48a) on the other side of the test portion. In any embodiment, the dried composition 50 may be coated on the entire circumference of the test portion.

Without being bound by theory, it is believed the presence of dried composition 50 in at least a portion of the at least one cavity 48a poses a greater challenge to a decontamination (e.g., washing) process than, for example, a substantially flat coupon coated with a test soil. Therefore, a teat element comprising the test portion 44a provides an ability to distinguish between various possible failure modes of the decontamination process.

A person having ordinary skill in the art will recognize a variety of design configurations can be used for the one or more cavity in the test element. For example, International Publication No. WO 2009/134509, which is incorporated herein by reference in its entirety, discloses a variety of sample acquisition elements comprising cavities that are suitable for use as in a test portion 44a of a test element 43. International Publication No. WO 93/00994, which is incorporated herein by reference in its entirety, also discloses a sample acquisition element with a plurality of grooves capable of retaining a sample. One or more of the grooves described therein could be used in a test element according to the present disclosure.

Figure 3A:
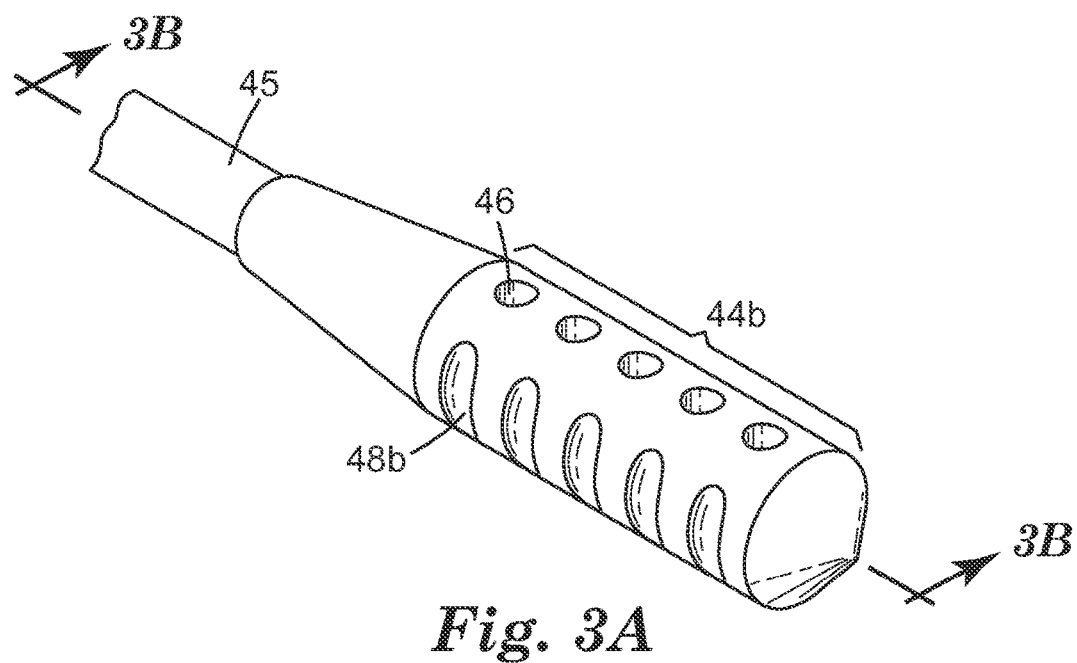
FIG. 3A is a perspective view, partially in section, of an alternative embodiment of a test portion comprising at least one cavity according to the present disclosure.
Figure 3B:
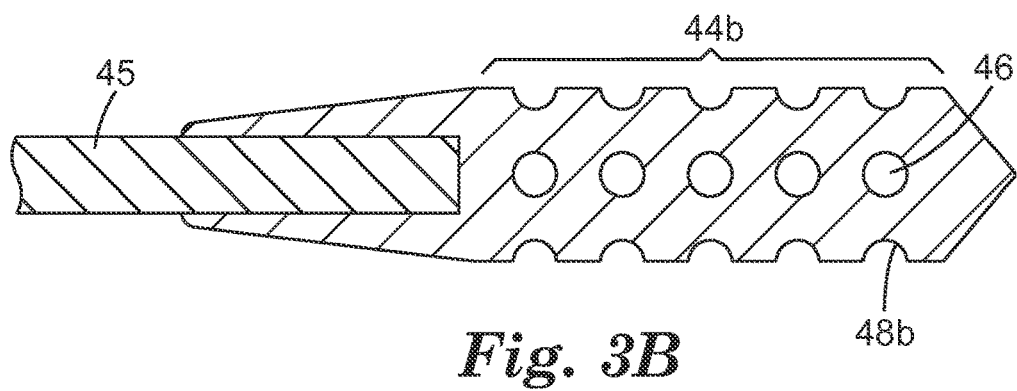
FIG. 3B is a cross-sectional side view of the test portion of FIG. 3A.

FIGS. 3A-3B show another embodiment of a test portion 44b with 3-dimensional structural features. In this embodiment, the test portion 44b comprises a plurality of cavities 48b and through-holes 46. The stem 45 and test portion 44b can be formed using the same materials and processes described above. In contrast to the cavities 48a of the test portion 44a described above, in this embodiment, the cavities 48b do not extend around the circumference of the test portion 44b. Without being bound by theory, it is believed the presence of dried composition 50 in at least a portion of at least one cavity 48b or at least one through-hole 46 poses a different challenge to a decontamination (e.g., washing) process than, for example, a substantially flat coupon coated with a test soil. Therefore, a test element comprising the test portion 44b provides an ability to distinguish between various possible failure modes of the decontamination process.

Figure 4A:
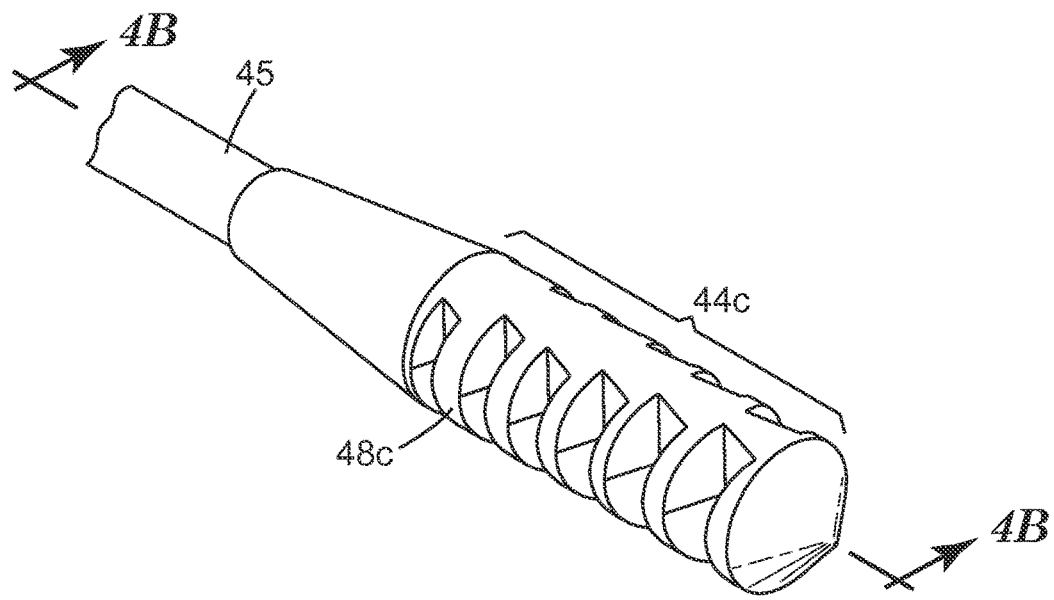
FIG. 4A is a perspective view, partially in section, of another alternative embodiment of a test portion comprising at least one cavity according to the present disclosure.
Figure 4B:
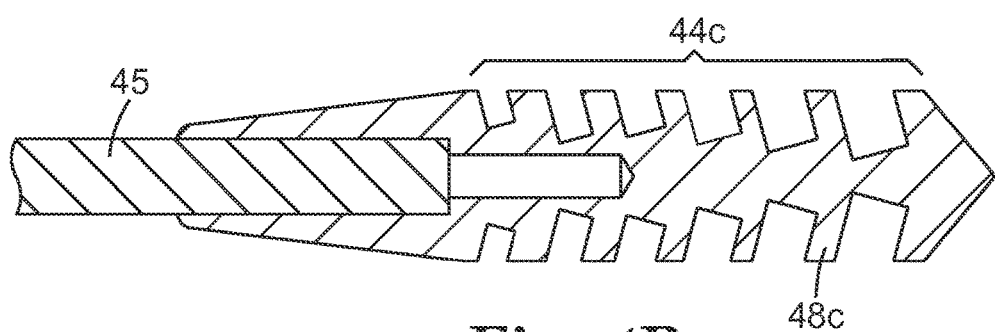
FIG. 4B is a cross-sectional side view of the test portion of FIG. 4A.

FIGS. 4A-4B show another embodiment of a test portion 44c with 3-dimensional structural features. In this embodiment, the test portion 44c comprises a plurality of spaced-apart cavities 48c. The stem 45 and test portion 44c can be formed using the same materials and processes described above. Without being bound by theory, it is believed the presence of dried composition 50 in at least a portion of the at least one cavity 48c poses a different challenge to a decontamination (e.g., washing) process than, for example, a substantially flat coupon coated with a test soil. Therefore, a test element comprising the test portion 44c provides an ability to distinguish between various possible failure modes of the decontamination process.

Figure 5A:
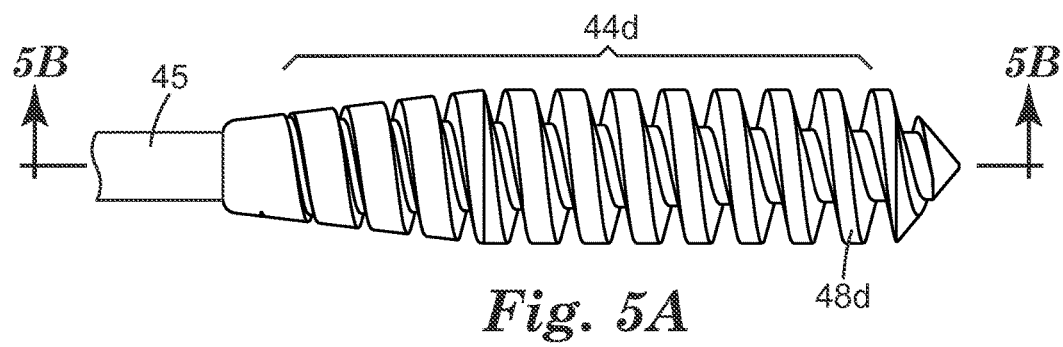
FIG. 5A is a side view, partially in section, of another alternative embodiment of a test portion comprising at least one cavity according to the present disclosure.
Figure 5B:
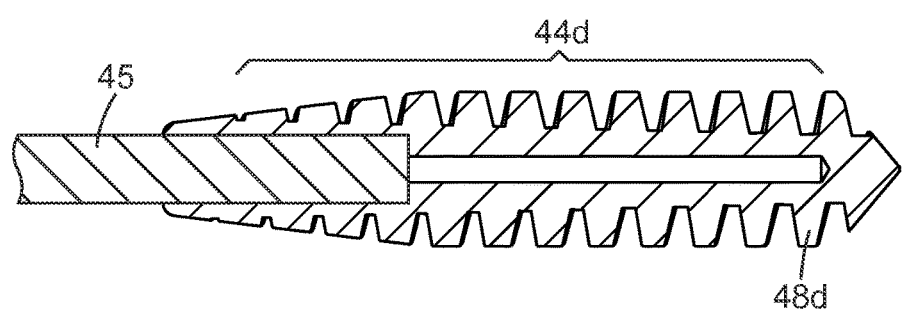
FIG. 5B is a cross-sectional side view of the test portion of FIG. 5A.

FIGS. 5A-5B show another embodiment of a test portion 44d with a 3-dimensional structural feature. In this embodiment, the test portion 44d comprises a spiral-shaped cavity 48d that extends along a longitudinal axis of the test portion. The stem 45 and test portion 44d can be formed using the same materials and processes described above. Without being bound by theory, it is believed the presence of dried composition 50 in at least a portion of the at least one spiral-shaped cavity 48d poses a different challenge to a decontamination (e.g., washing) process than, for example, a substantially flat coupon coated with a test soil. Therefore, a test element comprising the test portion 44d provides an ability to distinguish between various possible failure modes of the decontamination process.

FIG. 6 shows one embodiment of a test portion 44e that is substantially free of cavities. The stem 45 and test portion 44e can be formed using the same materials and processes described above. This test portion 44e can be used in a test element coated with the dried composition 50 of the present disclosure to monitor the efficacy of a decontamination process (e.g., the ability of the process to remove test soil from a substantially flat surface.

In any embodiment, the test element may be configured to actuate (i.e., open) the frangible seal. Referring back to FIG. 1, the test element 40 comprises a piercing tip 52 that is shaped to puncture a frangible seal. Alternatively or additionally, the stem 45 of any test element can be formed from a material (e.g., wood, metal, plastic) that is rigid enough such that when the test portion 44a, regardless of its shape, is urged against a frangible seal, the force of the test portion 44a against the seal can deform and/or rupture the frangible seal.

In any embodiment, the test portion of the test element can be shaped like a medical instrument or a part thereof. Advantageously, when the device of this embodiment is used to assess the efficacy of a decontamination process, the decontamination process is challenged to remove material (i.e., the dried composition) from an object that may be similar to the actual medical instruments that are cleaned in the automated washer. In some embodiments, the test portion may comprise a hinge structure (e.g., a hinge structure found on a scissors or a medical clamp). Advantageously, in these embodiments, the removal of the dried composition from the test portion more closely resembles actual conditions in a cleaning process.

The dried composition is releasably adhered to the test portion of the test element. The dried composition is dispersible in an aqueous solvent (e.g. the aqueous solvent used in a decontamination process). At least one or all of the components of the dried composition are water-soluble. The dried composition comprises a tracer analyte. The tracer analyte is dispersible, and may be soluble, in an aqueous solvent (e.g. the aqueous solvent used in a decontamination process). A "tracer analyte", as used herein comprises a compound that can be quantitatively detected using a photo-optical device. The detection may be achieved by direct detection (e.g., using an optical property of the tracer analyte per se such as, for example the U.V-visible absorbance of the tracer analyte) or by indirect detection (e.g., using an optical property of a derivative or byproduct of the tracer analyte). In any embodiment, the tracer analyte can be a chemical compound that is capable of participating in a chemical reaction that, either directly or indirectly, results in a detectable product. "Chemical reaction", as used herein, includes binding reactions (e.g., ionic binding, covalent binding, or hydrophobic interaction), synthetic reactions, decomposition reactions, oxidation reactions, reduction reactions, complexation reactions, acid-base reactions, and photochemical reactions.

By way of example, in one embodiment, the tracer analyte comprises an unlabeled protein (e.g., bovine serum albumin) In this embodiment, the tracer analyte can be detected indirectly by reacting the tracer analyte with a protein-detecting detection reagent such as bicinchoninic acid, for example, thereby forming a byproduct (i.e., a purple-colored bicinchoninic acid-$Cu^{1+}$ chelate), which can be quantitated using a spectrophotometer device.

By way of example, in another embodiment, the tracer analyte can comprise a labeled protein that undergoes a chemical reaction (e.g., a binding reaction, a hydrolytic reaction) to bind, release, or detectably modify the label and/or the labeled protein.

By way of example, in yet another embodiment, the tracer analyte comprises adenosine-5'-triphosphate (ATP) or a molecule (e.g., ADP) that can be converted to ATP (e.g., via adenylate kinase). In this embodiment, the ATP can be quantitatively detected, for example, by reacting it with luciferin and luciferase to cause the emission of a byproduct (light), which can be detected quantitatively using a luminometer. A person having ordinary skill in the art will recognize other compounds that are suitable for use as a tracer analyte and the particular detection reagent(s) and/or device(s) that can be used to detect and quantitate the tracer analyte. Preferred tracer analytes, have a relatively large dynamic range (e.g., about 4-$LOG_{10}$ range, about 5-$LOG_{10}$ range, about 6-$LOG_{10}$ range) of quantitative or semi-quantitative detection.

In any embodiment, the tracer analyte can be selected from the group consisting of an acid, a base, a nucleotide, a protein, a nucleic acid, or a nucleotide. The acid may comprise an organic acid (e.g., a fatty acid). The base may comprise an organic base (e.g., a basic amino acid such as arginine or lysine). The acid or base tracer analyte may be detected by U.V-visible absorbance or a pH-detecting detection reagent (e.g., a pH indicator) and quantitating the acid or base using a spectrophotometer, for example.

In any embodiment, the dried composition further may comprise biological materials that are found in animal tissue, fluids, and/or excreta. Nonlimiting examples of said biological materials include blood cells, serum proteins (e.g., albumin), bilirubin, a source of lipids (e.g., butter), mucin, and carbohydrates.

In any embodiment, the dried composition further may comprise a dye that is visually detectable prior to exposing the test element to a decontamination process. Accordingly, the dye can permit visual confirmation that the test element has the dried composition coated thereon.

In addition to the tracer analyte (e.g., an adenine nucleotide), the dried composition comprises a mixture having a predefined mass ratio of a polysaccharide (e.g., a cellulose polymer) and, optionally, a sugar (e.g., sucrose). Without being bound by theory, it is believed the cellulose polymer provides a binder for the composition and also inhibits dispersion of the tracer analyte when the test composition is contacted with an aqueous solvent. In addition, without being bound by theory, it is believed the hygroscopic nature of the sugar, when present, functions to prevent the mixture from becoming so dry that it could fracture and form flakes that could separate easily from the test portion during storage and/or transport of the device.

The test composition can be prepared as a liquid mixture and coated onto the test element as described herein. Table 1 shows a list of components and their respective dry weight percentages in a dried composition according to the present disclosure. In addition to a cellulose polymer (carboxymethylcellulose) and an adenine nucleotide (adenosine-5'-triphosphate), the list includes optional components such as proteins (albumin and hemoglobin), lipids (butter), and a visual indicator (red dye #40). In any embodiment wherein the composition comprises a sugar, the sugar and the cellulose polymer are present in the dried composition at a sugar:cellulose polymer mass ratio of about 9:1 to about 60:1, inclusive.

TABLE 1

Exemplary components of an aqueous mixture used to coat an article when forming an artificial test soil dried composition according to the present disclosure.

| Component | Dry Weight % |
|---|---|
| Carboxymethylcellulose | 1.5-59 |
| Sucrose | 0-95 |
| Albumin | 2.8-45 |
| Hemoglobin | 0.28-0.4.3 |
| Butter | 0.09-1.4 |
| Red Dye #40 | 0.05-0.75 |
| Adenosine-5'-triphosphate | 0.003-0.05 |

In any embodiment, the dried composition optionally may comprise a polymeric binder. Advantageously, the polymeric binder inhibits the dispersion of the tracer analyte in an aqueous solvent. Without being bound by theory, this inhibition occurs because the polymeric binder acts as a diffusion barrier to inhibit the release of the tracer element from the test portion. The polymeric binder rehydrates and dissolves and/or disperses into an aqueous washing solvent relatively slowly compared to the tracer analyte.

In any embodiment, the polymeric binder may comprise a cellulose polymer. In any embodiment, the cellulose polymer can be a water-soluble cellulose polymer (e.g., carboxymethyl cellulose, methyl cellulose, hydroxyethyl cellulose, carboxypropyl cellulose, hydroxyethyl methyl cellulose, hydroxypropyl methyl cellulose, and a combination of any two or more of the foregoing cellulose derivatives). The cellulose polymer can be prepared as an aqueous solution or aqueous suspension comprising the tracer analyte (e.g., 1 microgram/mL ATP), which is coated onto the test element and dried, as described herein. In any embodiment, the cellulose polymer-containing aqueous solution may comprise about 0.35 weight percent to about 1.47 weight percent cellulose polymer (e.g., carboxymethylcellulose).

The molecular weight of the polymeric binder can be selected such that the binder is more or less soluble in the liquid used in the decontamination process. For a given coating weight, higher molecular weight binders may be used to produce test soil compositions that are more difficult to wash off. Conversely, for a given coating weight, lower molecular weight binders may be used to produce test soil compositions that are less difficult to wash off.

The liquid used to coat the components of the test soil composition onto the test potion of a test element can be prepared as an aqueous solution or suspension comprising the adenine nucleotide tracer analyte. In any embodiment, the aqueous liquid can comprise adenosine-5'-triphosphate (ATP) as the adenine nucleotide tracer analyte. In any embodiment, the adenine nucleotide-containing aqueous solution may comprise about 3.0 μg/mL to about 45.0 μg/mL ATP as the adenine nucleotide tracer analyte.

In any embodiment, the dried composition may be prepared as a homogeneous mixture in a suitable solvent (e.g., water and/or an alcohol). In any embodiment, the dried composition may be dissolved or suspended in an organic solvent before it is applied to the test element. Advantageously, this may permit the application of higher concentrated solutions of tracer analyte (or other components (e.g., protein, lipid) of the dried composition) wherein the tracer analyte and/or component in the organic solvent is dissolved at a concentration that exceeds the water solubility of the tracer analyte or component.

In any embodiment, the dried composition can be applied as a single solution and/or suspension to the test portion of the test element (e.g., using processes described herein) in a single application. Alternatively, the dried composition can be applied to the test portion of the test element as two or more separate solutions and/or suspensions. For example, a first solution and/or suspension comprising the tracer analyte may be applied to the test element and a second solution and/or suspension comprising a polymeric binder may be applied separately to the test element. Optionally, the first solution and/or suspension may be permitted to dry or partially dry before the second solution and/or suspension is applied. Optionally, the first solution and or suspension can be identical to the first solution and or suspension.

Figure 7A:
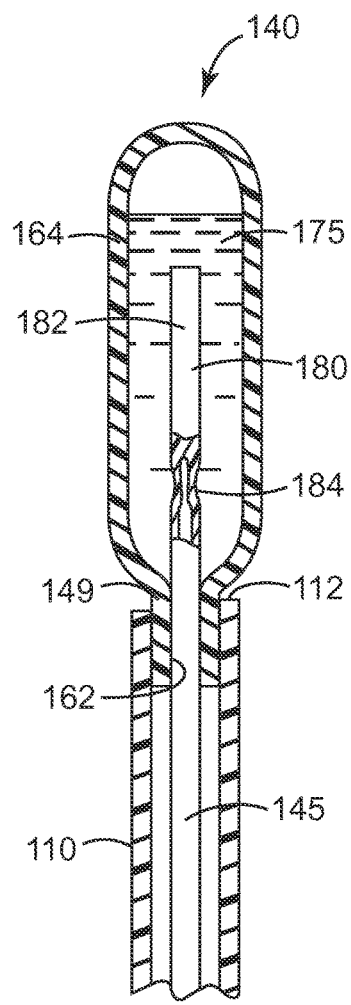
FIG. 7A-C are side views, partially in section, of a portion of one embodiment of an alternative test element comprising a hollow stem, a deformable reservoir, and a breakable valve that places the reservoir in selective fluid communication with the stem, showing how deformation of the reservoir causes breakage of the valve permitting the flow of a liquid into the stem.
Figure 7B:
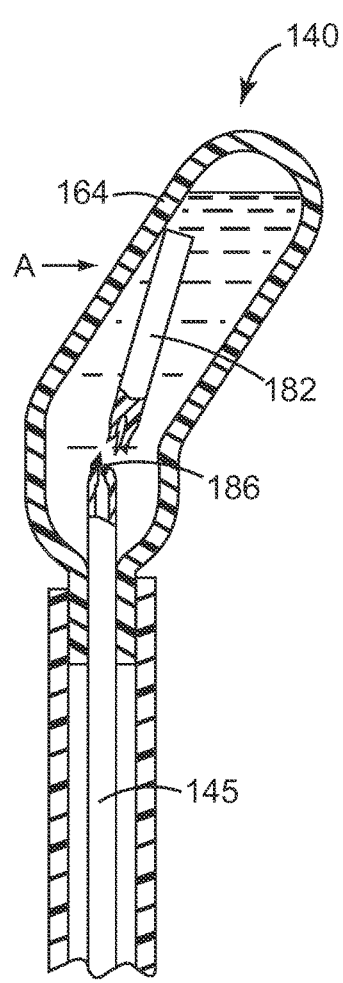
Figure 7C:
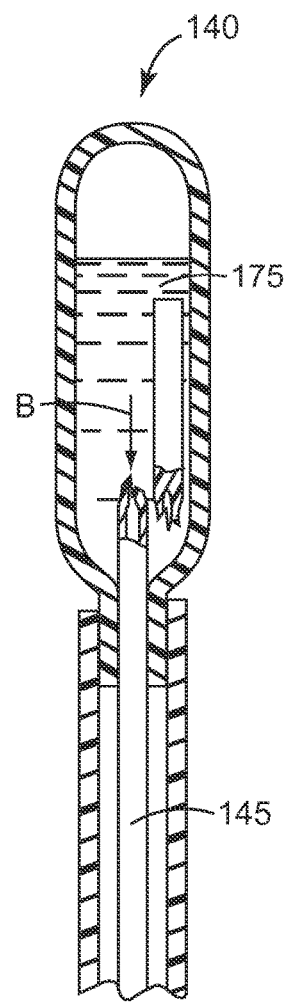

In any embodiment, the device can comprise a test element that is adapted to deliver a liquid to the container. Nason (U.S. Pat. No. 5,266,266; which is incorporated herein by reference in its entirety) discloses a specimen test unit that includes a swab member that can be adapted to function as a test element according to the present disclosure. FIGS. 7A-C show a portion (i.e., the portion proximate the first end 112 of the container 110) of one embodiment of a test element 140 that is adapted to deliver a second solvent 175 to the container 110. In this embodiment, the handle 149 comprises a hollow channel 162 extending there through. Coupled to the handle 149 (e.g., via an adhesive (not shown) or by friction fit) is a reservoir 164 with a hollow stem 145 coupled thereto (e.g. by friction-fit).

A portion 180 of the hollow stem 145 disposed in the reservoir 164 comprises a liquid flow regulator (e.g., a breakable liquid flow regulator) capable of placing the reservoir in fluid communication with the hollow stem 145. The portion 180 includes a solid rod segment 182 and a score 184 that facilitates the breakage of the stem 145, thereby creating a stem opening 186 to permit liquid flow through out of the reservoir through the hollow stem 145. The test element 140 can be made as described by Nason. As shown in FIG. 7B, (e.g., manual pressure) pressure against the flexible reservoir 164 in the direction of arrow "A" causes the reservoir 164 to deflect against the rod segment 182, causing the score 184 to fracture and optionally separate from the hollow stem 145 (as shown in FIG. 7C), which permits the flow of second solvent 175 through the stem opening 186 and into the hollow stem 145, as shown by arrow "B". A person having ordinary skill in the art will recognize other liquid flow regulator means (e.g., frangible ampoules and other means disclosed in U.S. Pat. Nos. 4,978,504 and 5,879,635, which are incorporated herein by reference in their entirety) that can be used to place the second solvent 175 in the reservoir 164 into fluid communication with the hollow stem 145.

In any embodiment, the second solvent 175 can be a liquid in which a portion (e.g., the tracer analyte) or all of the dried composition (not shown) is soluble. In any embodiment, the second solvent 175 may comprise water. In some embodiments, the second solvent 175 additionally comprises a buffer component to maintain the solvent within a predefined pH range (e.g., a pH range that is suitable for a reaction used in the detection of the tracer analyte). In some embodiments, the solvent may comprise a surfactant (e.g., a nonionic surfactant) to facilitate the dispersion of the tracer analyte and/or dried composition 50 into the second solvent 175. A suitable surfactant does not substantially interfere with a reaction, a detection reagent, and/or instrument that is used for the detection of the tracer analyte. In any embodiment the second solvent 175 may be the same as the first solvent (not shown), if present in the device.

Figure 8:
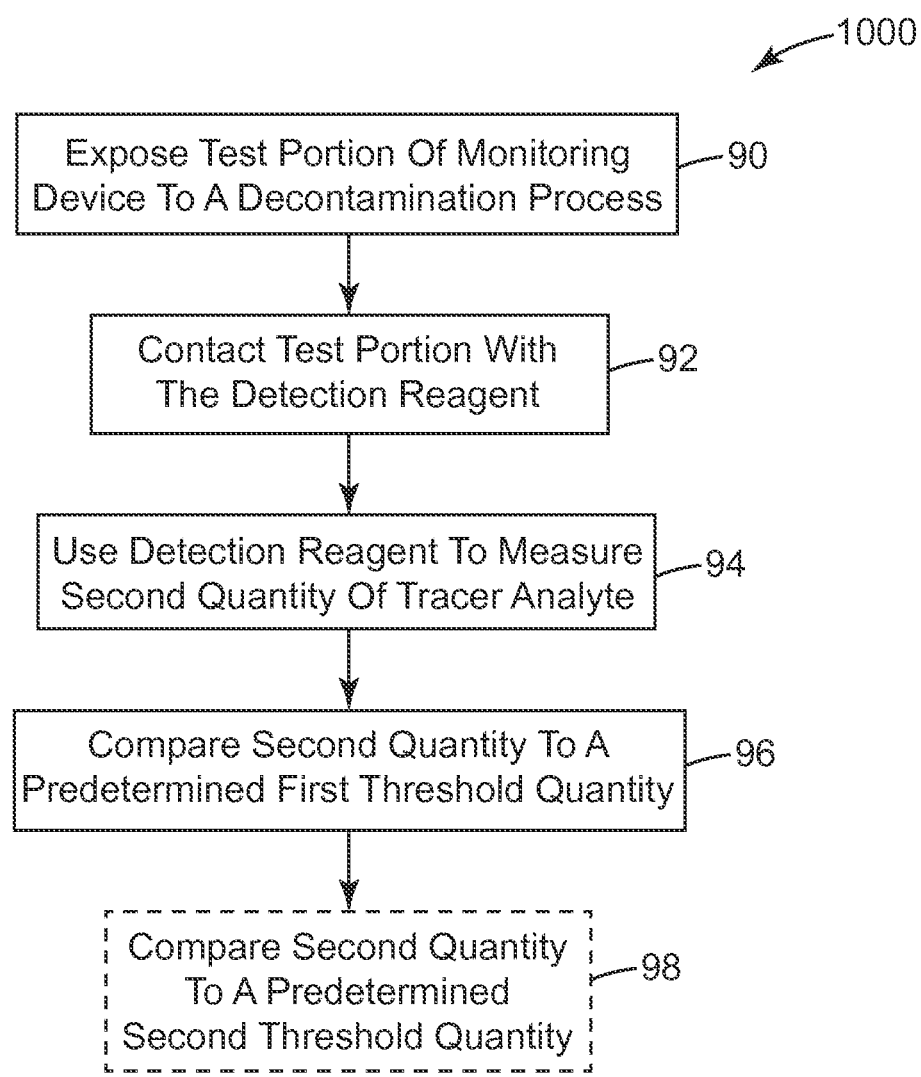
FIG. 8 is a block diagram of one embodiment of a method of assessing the efficacy of a washing process according to the present disclosure.

The present disclosure provides a method. For example, the present disclosure provides a method of assessing the efficacy of a decontamination process. FIG. 8 shows a block diagram of one embodiment of a method of assessing the efficacy of a decontamination process according to the present disclosure. The method 1000 comprises the step 90 of exposing to the decontamination process the test portion of any embodiment of a monitoring device according to the present disclosure. The test portion comprises a predefined first quantity of tracer analyte (e.g., an adenine nucleotide), as described herein. The method 1000 further comprises the step 92 of contacting the test portion of the test element with the detection reagent. In any embodiment, the contacting step 92 can take place in the container of the monitoring device, for example. The method 1000 further comprises the step 94 of using the detection reagent to measure a second quantity of the tracer analyte. The second quantity of tracer analyte refers to the measured amount of tracer analyte remaining on the test portion after the test portion was exposed to the decontamination process, as described herein. The method 1000 further comprises the step 96 of comparing the second quantity to a predetermined first threshold quantity.

A person having ordinary skill in the art will readily recognize a suitable method of measurement will depend upon the tracer analyte to be measured. In any embodiment, the tracer analyte is detected by a reaction of the tracer analyte with the detection reagent that results in the product or formation of a detectable product. In any embodiment, the detectable product can be a colored compound (e.g., a bicinchoninic acid-Cu+ chelate formed by the reaction of protein with Cu2+ in the presence of bicinchoninic acid) having a detectable absorbance spectrum. In these embodiments, the detectable product can be detected using a spectrophotometer, for example. In any embodiment, using an analytical instrument to detect a presence or an absence of the detectable product can comprise inserting at least a portion (e.g., a cuvette portion) of the container of the test device into the analytical instrument. In any embodiment, the detectable product can be electromagnetic radiation (e.g., visible light, such as the light emitted by the reaction of luciferin and luciferase with ATP, for example) having a certain wavelength (e.g., about 550 nm to about 620 nm).

The first threshold quantity defines an acceptable amount of tracer analyte that may remain on the monitoring device after the device is exposed to a decontamination process that is efficacious for removing biological residues from medical instruments or devices.

Exposing the test portion of the monitoring device to the decontamination process can comprise placing the test portion into an automated washer. In any embodiment, the automated washer can comprise an automated washer disinfector such as a GETINGE 46-series washer disinfector (available from Getinge USA, Inc., Rochester, N.Y.), for example. During normal handling and use, the test element of the monitoring device typically is grasped and/or secured (e.g., in the washer) preferably using its handle, if present, or its stem. In any embodiment, the test element can be placed in a rack, which is placed in the automated washer prior to exposing the test portion to the decontamination process. Optionally, the test element can be secured to the rack or to a structure (e.g., a rack or shelf) in the automated washer.

Figure 12:
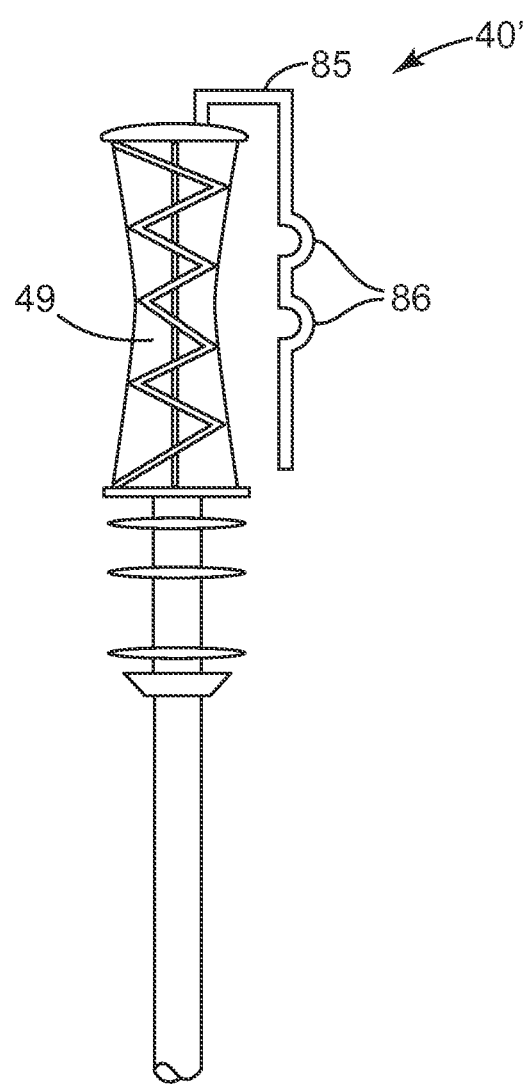
FIG. 12 is a side view of the handle portion of one embodiment of a test device comprising a secural element according to the present disclosure.

In any embodiment, the test element further may comprise a secural structure configured to detachably secure the test element to a structure (e.g., a rack or shelf) in the automated washer. FIG. 12 shows a portion (i.e., the portion proximate the handle) of one embodiment of test element 40' comprising a secural element 85. In some embodiments, the secural element 85 may be formed (e.g., by a molding process) of the same material as the handle 49. The secural element 85 can be shaped and dimensioned to include one or more engagement structures 86 that can releasably hold a portion of an automated washer rack or wire basket, for example, and thereby hold the test device at a fixed location within an automated washer. In some embodiments, the secural element 85 can be formed separately and attached to the test element 40' using an attachment means known in the art (e.g., an adhesive, a thermal bond, an ultrasonic weld, a screw, a rivet, or the like). The secural element can be fabricated from any material that is not substantially degraded by a decontamination process. Non-limiting examples of suitable materials include metal and polymeric (e.g., polypropylene, polyethylene) materials.

Securing the test element may be performed using a zip-tie, a clamp (e.g., a hose clamp), or the like. In any embodiment, the test portion may be placed in the automated washer at a peripheral location within the washing chamber, thereby testing the efficacy of the decontamination process in a location within the washing chamber that is relatively difficult for a fluid stream emitted by the washer to reach. The location may be particular difficult for the fluid stream to reach if the washer malfunctions (e.g., due to abnormally-low water pressure.

Many commercial automated washers that are used for decontaminating instruments and devices are programmable and are configured with preset decontamination processes that include one or more washing sub-processes ("steps"); optionally, one or more rinse subprocesses ("steps"); and optionally, one or more drying sub-process ("step"). Accordingly, exposing the test portion of the test element to the decontamination process can comprise placing the test portion into an automated washer and performing at least a portion of an automated decontamination process while the test portion is disposed in the automated washer. An automated decontamination process may comprise, for example, one or more pre-rinse step, one or more wash step, one or more rinse step, one or more drying step, or a combination of any two or more of the foregoing steps. After exposing the test portion to at least a portion of the automated decontamination process, the amount of tracer analyte remaining on the test element can be analyzed to determine whether the decontamination process, or selected sub-processes thereof, removed any or all of the tracer analyte from the test element, thereby indicating the decontamination efficacy of the portion of the automated decontamination process.

In a preferred embodiment, exposing the test portion of the test element to the decontamination process comprises placing the test portion into an automated washer and performing a complete automated decontamination process while the test portion is disposed in the automated washer.

A non-limiting example of a preset automated decontamination process includes the following steps: a 1-minute pre-rinse step using cold water, a 5-minute washing step using hot (e.g., 60° C.) water mixed with an enzyme detergent (e.g., a multi-enzyme detergent), two 1-minute rinse steps with hot water, a 1-minute disinfection step with very-hot (e.g., 90° C.) deionized water, and a 10-minute drying step. Thus, after exposing the test portion to the complete automated decontamination process, the amount of tracer analyte remaining on the test element can be analyzed to determine whether the decontamination process removed any or all of the tracer analyte from the test portion of the test element.

Figures 9, 10:
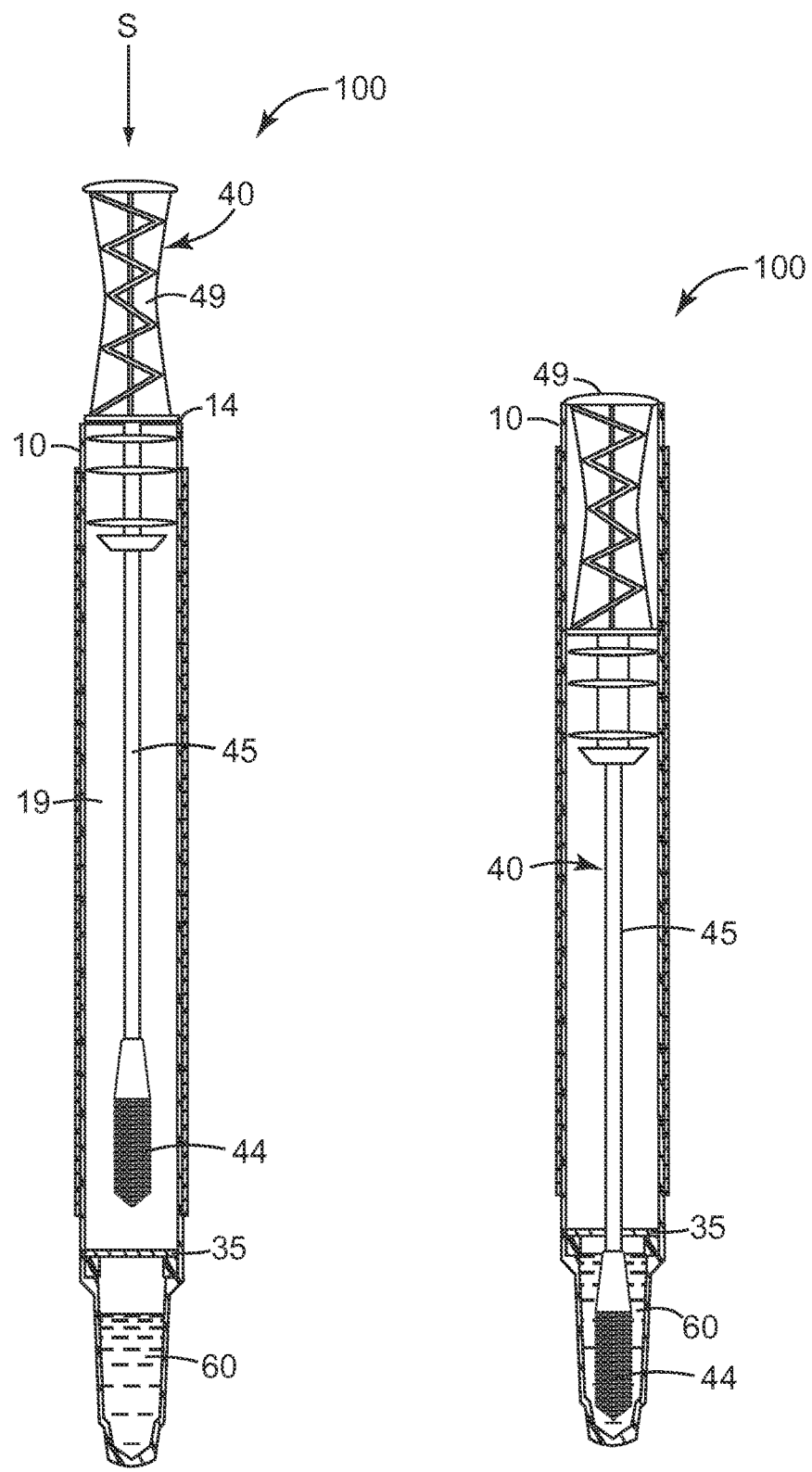
FIG. 9 is a side view, partially in section of the assembled device of FIG. 1 with the test element disposed in a first operational position with respect to the container.
FIG. 10 is a side view, partially in section of the assembled device of FIG. 1 with the test element disposed in a second operational position with respect to the container.

Typically, while the test portion is exposed to the decontamination process, the container of the monitoring device is kept in a location outside the automated washer. After the test portion has been exposed to the decontamination process, the test element can be removed (e.g., from the automated washer) and inserted into the receiving chamber of the container. FIG. 9 shows a side view, partially in section of one embodiment of a device 100 with the test element 40 inserted into the container. In the illustrated embodiment, the test element 40 is disposed in a first operational position with respect to the container 10. In the first operational position, a first portion of the test element (e.g., the test portion 44 and stem 45) are disposed in the receiving chamber 19 of the container 10 and a second portion of the test element (e.g., the handle 49) is operationally coupled (e.g., by friction fit) with the container 10 proximate the opening 14 of the container.

The method of the present disclosure comprises contacting the test portion of the test element with the detection reagent in the container of the test device. In the illustrated embodiment of FIGS. 9-10, this comprises moving (e.g., by applying manual pressure to the handle in the direction of arrow "S") the test element 40 into a second operational position with respect to the container 10, as shown in FIG. 10. In the second operational position, the test element 40 has pierced the frangible seal 35 and the test portion 44 is contacting the first solvent 60, in which the detection reagent (not shown) is dissolved. By way of example, the tracer analyte can be an adenine nucleotide (e.g., ATP) and the first solvent 60 may be an aqueous solution with a pH that is suitable to facilitate the reaction of a detection reagent (e.g., luciferase enzyme) with luciferin and the tracer analyte (ATP).

In any embodiment, contacting the test portion of the test element with the solvent in the container of the test device can further comprise dispersing and/or dissolving the tracer analyte and/or dried composition into the solvent.

In preferred embodiments of the method, the quantity of detectable product is proportional to the quantity of tracer analyte, if present, on the test element. In any embodiment, the measured second quantity can be a threshold detectable quantity, which simply indicates the presence or absence of the detectable product. A person having ordinary skill in the relevant art will recognize the threshold detectable quantity represents the lower limit of detection and is defined by several parameters including, for example, the reactants, the container, and the analytical instrument. In any embodiment, the measured second quantity can be an absolute quantity, which can be determined by comparing the detectable quantity to a standard or a plurality of standards, for example. In any embodiment, the measured second quantity can be a relative quantity (e.g., relative light units detected from a light-emitting reaction).

In any embodiment, a method of the present disclosure comprises a step of comparing the measured second quantity of tracer analyte to a plurality of threshold quantities. Thus, the method 1000 of FIG. 8 comprises the optional step 98 of comparing the measured quantity of the detectable product to a second threshold quantity. The second threshold quantity can be selected to indicate a quantity (e.g., a maximum quantity) of detectable product associated with a particular failure mode (e.g., inadequate wash sub-process or inadequate rinse sub-process) of the decontamination process. Thus, in these embodiments; when the decontamination process is inadequate to remove a sufficient quantity of soil (e.g., the tracer analyte) from the test element, the second quantity of tracer analyte may be greater than or equal to the second threshold quantity.

In another embodiment of the method, the standard may be a measurable quantity of tracer analyte that is detected from a test element (e.g., a "control" test element) that has not been exposed to a decontamination process. In this embodiment, an indication of exposure to an adequate decontamination process can be that the washed test element retains a predetermined percentage (e.g., less than or equal to 50%, less than or equal to 40%, less than or equal to 30%, less than or equal to 25%, less than or equal to 20%, less than or equal to 15%, less than or equal to 10%, less than or equal to 5%, less than or equal to 2%, less than or equal to 1%, less than or equal to about 2%, less than or equal to 0.1%,) of the quantity of tracer analyte that is detectable on a control test element (i.e., a test element that has not been exposed to the decontamination process.

In another embodiment of the method, the standard may be an arbitrary value (e.g., relative light units, micrograms of tracer analyte, or the like) that is selected (e.g., by the user or the provider of the test element) to indicate the efficacy of the decontamination process.

In any embodiment, an operator may desire to keep a record of the detection of a presence or measureable quantity of tracer analyte detected from a test element exposed to a particular decontamination process. In some embodiments, the record may be an electronic record that is stored on a computer-readable medium using electronic data storage processes that are well-known in the art. The computer-readable medium may comprise random access memory (RAM) such as synchronous dynamic random access memory (SDRAM), read-only memory (ROM), non-volatile random access memory (NVRAM), electrically erasable programmable read-only memory (EEPROM), FLASH memory, magnetic or optical data storage media, and the like.

In any embodiment of the method, an operator may desire to associate a first datum (e.g., the record of the detection of a presence or measureable quantity of tracer analyte detected from a test element) with a second datum (e.g., other information related to the test element). In any embodiment, the second datum comprises information selected from the group consisting of a date, a time, a washing apparatus, an operator, an instrument to be washed, and a combination of two or more of any of the foregoing test data. Advantageously, associating the first datum with the second datum can allow the operator to verify that a particular instrument was present in an automated washer with a test element that verified the efficacy of the decontamination process to which both the instrument and the test element were exposed.

In any embodiment of the method, exposing the test portion of a test element to a decontamination process can comprise exposing the test portions of a plurality of test elements to a decontamination process. Advantageously, this embodiment can be used to identify certain spatial regions within an automated washer that do not wash objects as effectively as other spatial regions within the automated washer. This type of information can be used by the operator to make decisions such as preventative maintenance schedules and/or load configurations, for example, for particular automated washers. In these embodiments, a first test device can be positioned at a first predefined location (e.g., upper rack proximate the back of the washer) and a second test device can be positioned at a second predefined location (lower rack proximate the front of the washer). After exposing the first and second test devices to a decontamination process, the tracer analyte remaining on the test portion of each test device is measured as described herein and each measured quantity can be compared to a control value (a first or second predetermined threshold value) and/or can be compared to each other. The control value may indicate the devices were exposed to an effective decontamination process or it may indicate the devices were exposed to an ineffective decontamination process. According to this embodiment, the method can be used to create a 2-dimensional or 3-dimensional map of the interior of an automated washer, the map showing specific regions of the washer and the decontamination efficacy of each region.

In any embodiment, the method optionally can comprise the step of placing the test portion of the device in a receiver configured to restrict fluidic accessibility to the test portion. In some embodiments, the receiver may comprise a wall that shields the test portion from a direct spray of wash solvent (e.g., water) emitted from a nozzle or orifice in the automated washer. Thus, in order for the wash solvent to impinge on the test portion, it must take an indirect path (e.g., by deflection off a wall or other object present in the automated washer. In some embodiments, placing the test portion of the monitoring device in a receiver configured to restrict fluidic accessibility to the test portion comprises placing the test portion into an interior space of an object having a lumen. Exemplary objects having lumens include, for example, tubes, endoscopes, bottles, portions thereof, and the like.

In another aspect, the present disclosure provides a method of processing an object to be decontaminated. The method comprises processing in one load in a decontamination process i) an object having an unknown amount of biological soil disposed thereon and/or therein and ii) a monitoring device according to any of the embodiments disclosed herein. After processing the load with the aforementioned items, the method comprises contacting the test portion of the test element with a detection reagent for detecting the tracer analyte of the monitoring device, as disclosed herein. The method further comprises using the detection reagent to measure a second quantity of tracer analyte remaining on the test portion and comparing the second quantity of the tracer analyte to a plurality of predetermined threshold quantities, as described herein. The plurality of predetermined threshold quantities can distinguish, for example, two distinct failure modes for the decontamination process. By way of example, the monitoring device can comprise ATP as the tracer analyte and the detection reagent can comprise luciferase and/or luciferin. In any embodiment, processing the object and the monitoring device in a decontamination process comprises processing the object and the monitoring device in an automated washer or an automated washer-disinfector. In any embodiment, processing as a single batch in a decontamination process the object and the monitoring device comprises processing as a single batch in a decontamination process the object and a plurality of the monitoring devices. In any embodiment, processing a plurality of monitoring devices comprises processing a first monitoring device at a first location and processing a second monitoring device at a second location that is spaced apart from the first location. In any embodiment, the plurality of threshold quantities comprises a first threshold quantity and the first threshold quantity is less than or equal to about 0.1% of the first quantity.

In any embodiment, the plurality of threshold quantities comprises a second threshold quantity and the second threshold quantity is about 1% of the first quantity.

In yet another aspect, the present disclosure provides an article comprising a test portion, the test portion having a dried composition adhered thereto. The dried composition comprises a cellulose polymer and a predetermined amount of a tracer analyte (e.g., an adenine nucleotide such as ATP), as described herein. In any embodiment, the dried composition optionally comprises a sugar. In any embodiment, the article is a test element as described herein. In any embodiment, the cellulose polymer comprises a water-soluble cellulose derivative. In any embodiment, the water-soluble cellulose derivative is selected from the group consisting of carboxymethyl cellulose, methyl cellulose, hydroxyethyl cellulose, carboxypropyl cellulose, hydroxyethyl methyl cellulose, hydroxypropyl methyl cellulose, and a combination of any two or more of the foregoing cellulose derivatives. In any embodiment wherein the composition comprises a sugar, the sugar comprises a monosaccharide or disaccharide (e.g., sucrose, glucose, lactose, galactose, maltose, and the like). In any embodiment, the composition further comprises a biological soil reagent selected from the group consisting of a protein, a lipid, hemoglobin, a dye, or a combination of any two or more of the foregoing biological soil reagents. In any embodiment, the sugar, when present, and the cellulose polymer are present in the dried composition at a sugar:cellulose polymer mass ratio of about 9:1 to about 60:1, inclusive. In any embodiment, the test portion comprises a surface area, wherein a portion of the surface area is disposed in at least one cavity.

In yet another aspect, the present disclosure provides a kit. The kit can comprise any embodiment of the monitoring device disclosed herein. In any embodiment, the kit further may comprise a means to secure a test element. The means to secure the test element may comprise a clamp, a string, a wire, a zip-tie, or any other suitable means capable of securing the test element to an object (e.g., a medical instrument, a shelf, a wire basket) in an automated washer.

Figure 11:
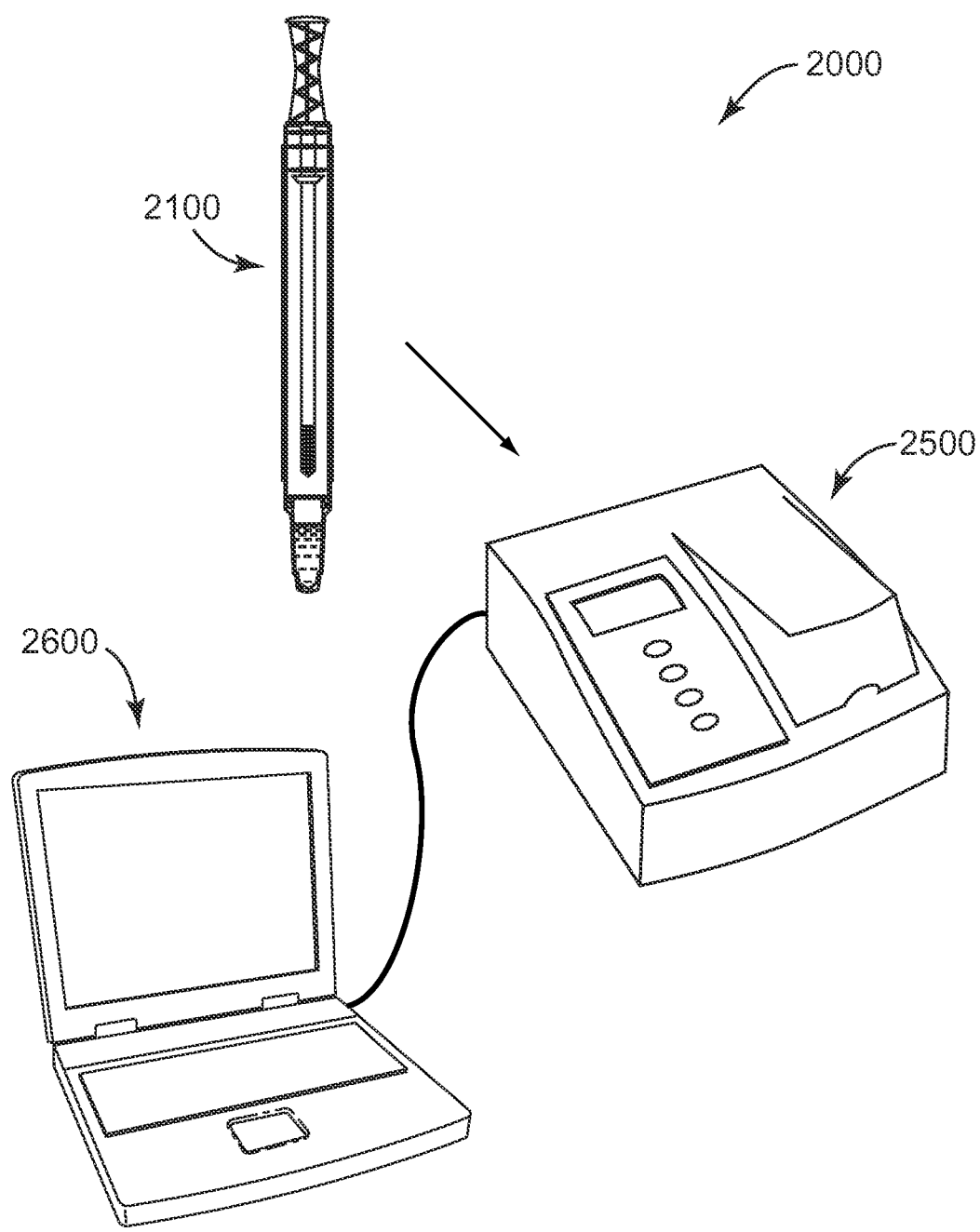
FIG. 11 is a schematic view of a system for assessing the efficacy of a washing process according to the present disclosure.

In another aspect, the present disclosure provides a system. The system can be used to test the efficacy of a decontamination process. The system comprises a monitoring device comprising a container and a test element according to any embodiment described herein. The test portion comprises a predetermined quantity of a tracer analyte releasably adhered thereto. The monitoring device includes a reagent for detecting the tracer analyte, as described herein. The system further comprises an analytical instrument capable of detecting a detectable product produced by a reaction between the tracer analyte and the detection reagent. In any embodiment, the system may further comprise a processor capable of receiving data from the analytical instrument and a memory (not shown) capable of storing the received data. FIG. 11 shows a schematic view of one embodiment of a system 2000 according to the present disclosure. The system comprises a device 2100 and an analytical instrument 2500 for analyzing the device (i.e., for detecting the tracer analyte). Optionally, the system 2000 further comprises a processor 2600.

Optionally, the processor 2600 may comprise software or firmware capable of operating the analytical instrument 2500. In any embodiment, the software may be adapted to facilitate the detection of the detectable product that indicates a presence of the tracer analyte. The processor 2600 may include memory and may create an information database in its memory to track and store such information. Processor 2600 may associate various types of information with the device 2100. Numerical values associated with one or more test elements may be analyzed and/or stored by processor 2600. In addition, a numerical value associated with a first test element can be analyzed by processor 2600 to compare the value to second test element and/or a control value (e.g., a first or second predetermined threshold value) associated with a standard (e.g., a positive control, a negative control).

Processor 2600 may execute software for analysis of test device 2100, and for database management consistent with the techniques known in the art. Accordingly, processor 2600 may also include memory to store the various types of information associated with a particular device 2100, the information being generated by the analytical instrument 2500. Processor 2600 may comprise a personal computer (PC), desktop computer, laptop computer, handheld computer, workstation, or the like.

In another aspect, the present disclosure provides a dried artificial test soil. The test soil is a composition comprising a tracer analyte (e.g., an acid, a base, a nucleotide, a protein, a nucleic acid, a carbohydrate, or hemoglobin) according to the present disclosure. In a preferred embodiment, the tracer analyte is an adenine nucleotide (e.g., Adenosine-5'-triphosphate). In any embodiment, the test soil composition further can comprise an optional dye in an amount sufficient to be optically detectable, as described herein. The test soil further comprises a polymeric binder (e.g., a cellulose polymer, as described herein). The dried test soil is prepared by dissolving and/or making a homogeneous dispersion of the tracer analyte, polymeric binder, and optional dye in a suitable solvent (e.g., water, alcohol, or mixtures thereof), applying the mixture to a surface (e.g., by spraying, dip-coating, or other coating processes known in the art) of a substrate, and removing at least a portion of the solvent (e.g., substantially all of the solvent) to obtain a dried coating on the substrate.

Without being bound by theory, the polymeric binder provides one or more of the following technical effects in the test soil composition: 1) the polymeric binder provides bulk mass that can facilitate the adherence of relatively small quantities of tracer analyte to a substrate, 2) the polymeric binder provides adhesive properties to facilitate the adherence of the test soil composition to the substrate, 3) the polymeric binder provides a solubility and/or diffusion barrier that prevents the substantially immediate dissolution and release of the tracer analyte from the substrate when the test soil is contacted with a solvent (e.g., water, hot water) in which the tracer analyte is soluble or dispersible and, 4) in the instance where the polymeric binder comprises a protein, the polymeric binder may provide some buffering capacity to maintain the pH of the composition.

Exemplary Embodiments

Embodiment A is a method of assessing the efficacy of a decontamination process, comprising:

exposing a test portion of a monitoring device to a decontamination process;

wherein the test portion includes a homogeneous, dried composition removably adhered thereto;

wherein the dried composition comprises a cellulose polymer and a predetermined first quantity of an adenine nucleotide;

after exposing the test portion to the decontamination process, contacting the test portion with a reagent for detecting the adenine nucleotide;

using the detection reagent to measure a second quantity of the adenine nucleotide remaining on the test portion; and comparing the second quantity to a predetermined first threshold quantity.

Embodiment B is the method of Embodiment A, wherein comparing the second quantity to a predetermined threshold quantity further comprises comparing the second quantity to a plurality of predetermined threshold quantities.

Embodiment C is the method of Embodiment B, further comprising the steps of comparing the second quantity of adenine nucleotide to a second threshold quantity and reporting an outcome of an assessment of the efficacy:

wherein, when the second quantity is less than or equal to the first threshold quantity, the outcome of the decontamination process is reported to indicate the process was efficacious;

wherein, when the second quantity is greater than the first threshold quantity but less than or equal to a second threshold quantity, the outcome of the decontamination process is reported to indicate the process had a deficiency associated with a first predetermined parameter of the decontamination process.

Embodiment D is the method of Embodiment C wherein, when the second quantity is greater than the second threshold quantity, the outcome of the decontamination process is reported to indicate the process had a deficiency associated with a second predetermined parameter of the decontamination process.

Embodiment E is the method of any one of preceding Embodiments, wherein exposing the test portion to the decontamination process comprises placing the test portion into an automated washer and performing at least a portion of an automated decontamination process while the test portion is disposed in the automated washer.

Embodiment F is the method of Embodiment E, wherein the automated washer comprises an automated washer-disinfector.

Embodiment G is the method of any one of the preceding Embodiments, wherein using the detection reagent to measure the second quantity comprises using an instrument to measure the second quantity.

Embodiment H is the method of any one of Embodiments E through G, wherein exposing the test portion of a monitoring device comprises exposing the test portion of a plurality of monitoring devices, wherein the method further comprises positioning a first monitoring device at a first predefined location in the automated washer and positioning a second monitoring device at a second predefined location in the automated washer.

Embodiment I is the method of Embodiment H, further comprising the step of comparing the second quantity of adenine nucleotide associated with the first monitoring device to the second quantity of adenine nucleotide associated with the second monitoring device.

Embodiment J is the method of any one of the preceding Embodiments, further comprising the step of placing the test portion of the monitoring device into a receiver configured to restrict fluidic accessibility to the test portion.

Embodiment K is the method of Embodiment J, wherein placing the test portion of the monitoring device into a receiver configured to restrict fluidic accessibility to the test portion comprises placing the test portion into an interior space of an object having a lumen.

Embodiment L is a method of processing an object to be decontaminated, comprising:

processing in one load in a decontamination process:

an object having an unknown amount of biological soil disposed thereon and/or therein;

a monitoring device comprising a test portion;

wherein the test portion includes a homogeneous, dried composition removably adhered thereto;

wherein the dried composition comprises a cellulose polymer and a predetermined first quantity of an adenine nucleotide;

after processing the batch in the decontamination process, contacting the test portion with a reagent for detecting the adenine nucleotide;

using the detection reagent to measure a second quantity of adenine nucleotide remaining on the test portion; and comparing the second quantity to a plurality of predetermined threshold quantities.

Embodiment M is the method of any one of the preceding Embodiments, wherein the dried composition further comprises a sugar.

Embodiment N is the method of Embodiment L or Embodiment M, wherein processing the object and the monitoring device in a decontamination process comprises processing the object and the monitoring device in an automated washer or an automated washer-disinfector.

Embodiment O is the method of any one of Embodiments L through N, wherein processing in one load in a decontamination process the object and the monitoring device comprises processing in one load in a decontamination process the object and a plurality of the monitoring devices.

Embodiment P is the method of Embodiment O, wherein processing a plurality of monitoring devices comprises processing a first monitoring device at a first location and processing a second monitoring device at a second location that is spaced apart from the first location.

Embodiment Q is the method of any one of the preceding Embodiments, wherein the plurality of threshold quantities comprises a first threshold quantity, wherein the first threshold quantity is less than or equal to about 0.1% of the first quantity.

Embodiment R is the method of any one of the preceding Embodiments, wherein the plurality of threshold quantities comprises a second threshold quantity, wherein the second threshold quantity is about 1% of the first quantity.

Embodiment S is a monitoring device, comprising:

a container comprising a first end with an opening dimensioned to receive a test element;

a test element disposed in the container, the test element comprising a test portion;

a dried composition releasably adhered to the test portion, the dried composition comprising a cellulose polymer and a predetermined quantity of an adenine nucleotide; and a reagent for detecting the adenine nucleotide, the reagent disposed in the container.

Embodiment T is the monitoring device of Embodiment S, wherein the dried composition further comprises a sugar.

Embodiment U is the monitoring device of Embodiment S or Embodiment T, wherein the cellulose polymer comprises a water-soluble cellulose derivative.

Embodiment V is the monitoring device of Embodiment U, wherein the water-soluble cellulose derivative is selected from the group consisting of carboxymethyl cellulose, methyl cellulose, hydroxyethyl cellulose, carboxypropyl cellulose, hydroxyethyl methyl cellulose, hydroxypropyl methyl cellulose, and a combination of any two or more of the foregoing cellulose derivatives.

Embodiment W is the monitoring device of any one of Embodiments S through V, wherein the sugar comprises sucrose.

Embodiment X is the monitoring device of any one of Embodiments S through W, wherein the composition further comprises a biological soil reagent selected from the group consisting of a protein, a lipid, hemoglobin, a dye, or a combination of any two or more of the foregoing biological soil reagents.

Embodiment Y is the monitoring device of any one of Embodiments S through X, wherein the sugar and the cellulose polymer are present in the composition at a sugar:cellulose polymer mass ratio of about 9:1 to about 60:1, inclusive.

Embodiment Z is the monitoring device of any one of Embodiments S through Y, wherein the test portion comprises a surface area, wherein a portion of the surface area is disposed in at least one cavity.

Embodiment AA is the monitoring device of any one of Embodiments S through Z, further comprising a frangible seal, wherein a receiving chamber is disposed on a first side of the frangible seal proximate the opening and a cuvette chamber is disposed on a second side of the frangible seal distal the opening.

Embodiment BB is the monitoring device of Embodiment AA, wherein the test element is configured to disrupt the frangible seal.

Embodiment CC is monitoring device of any one of Embodiments S through BB, wherein the container comprises a cuvette portion configured to be operationally coupled with the analytical instrument.

Embodiment DD is the monitoring device of any one of Embodiments S through CC, further comprising a secural element.

Embodiment EE is a kit, comprising the monitoring device of any one of Embodiments S through DD.

Embodiment FF is the kit of Embodiment EE, further comprising an analytical instrument for quantifying the adenine nucleotide.

Embodiment GG is the kit of Embodiment EE or Embodiment FF, further comprising a means to secure a test element.

Embodiment HH is the kit of any one of Embodiments EE through GG, further comprising an article comprising a receiver dimensioned to receive the test element and to restrict fluidic accessibility to the test portion.

Embodiment II is the kit of Embodiment HH, wherein the article is an object having a lumen.

Embodiment JJ is an article comprising a test portion, the test portion having a dried composition removably adhered thereto; wherein the dried composition comprises a cellulose polymer, and a predetermined amount of an adenine nucleotide.

Embodiment KK is the article of Embodiment JJ, wherein the dried composition further comprises a sugar.

Embodiment LL is the article of Embodiment JJ or Embodiment KK, wherein the cellulose polymer comprises a water-soluble cellulose derivative.

Embodiment MM is the article of Embodiment LL, wherein the water-soluble cellulose derivative is selected from the group consisting of carboxymethyl cellulose, methyl cellulose, hydroxyethyl cellulose, carboxypropyl cellulose, hydroxyethyl methyl cellulose, hydroxypropyl methyl cellulose, and a combination of any two or more of the foregoing cellulose derivatives.

Embodiment NN is the article of any one of Embodiments JJ through MM, wherein the sugar comprises sucrose.

Embodiment OO is the article of any one of Embodiments JJ through NN, wherein the composition further comprises a biological soil reagent selected from the group consisting of a protein, a lipid, hemoglobin, a dye, or a combination of any two or more of the foregoing biological soil reagents.

Embodiment PP is the article of any one of Embodiments JJ through OO, wherein the sugar and the cellulose polymer are present in the dried composition at a sugar:cellulose polymer mass ratio of about 9:1 to about 60:1, inclusive.

Embodiment QQ is the article of any one of Embodiments JJ through PP, wherein the test portion comprises a surface area, wherein a portion of the surface area is disposed in at least one cavity.

Embodiment RR is a system, comprising:
 a monitoring device, comprising:
  a container comprising a first end with an opening dimensioned to receive a test element;
  a test element disposed in the container, the test element comprising a test portion;
  a dried composition releasably adhered to the test portion, the dried composition comprising a cellulose polymer and a predetermined quantity of an adenine nucleotide;
  a reagent for detecting the adenine nucleotide, the reagent disposed in the container;
 an analytical instrument for detecting a reaction between the adenine nucleotide and the reagent; and
 a processor configured to receive electronic data from the analytical instrument and to process or report the data.

Embodiment SS is the system of Embodiment RR, wherein the dried composition further comprises a sugar.

Embodiment TT is a method of assessing the efficacy of a decontamination process, the method comprising:
 exposing a test portion of a monitoring device to a decontamination process;
  wherein the test portion includes a dried composition removably adhered thereto;
  wherein the dried composition comprises a cellulose polymer and a predetermined first quantity of a tracer analyte;
 after exposing the test portion to the decontamination process, contacting the test portion with a reagent for detecting the tracer analyte;
 using the detection reagent to measure a second quantity of tracer analyte remaining on the test portion; and
 comparing the second quantity to a plurality of predetermined threshold quantities;
 wherein a second quantity less than or equal to a first threshold quantity indicates the decontamination process was efficacious;
 wherein a second quantity greater than the first threshold quantity, but less than or equal to a second threshold quantity, indicates a deficiency of a first predetermined parameter of the decontamination process;
 wherein a second quantity greater than the second threshold quantity indicates a deficiency of a second predetermined parameter of the decontamination process.

Embodiment UU is a method of processing an object to be decontaminated, the method comprising:
 processing in one load in a decontamination process:
  an object having an unknown amount of biological soil disposed thereon and/or therein;
  a monitoring device comprising a test portion;
   wherein the test portion includes a dried composition removably adhered thereto;

wherein the dried composition comprises a cellulose polymer and a predetermined first quantity of a tracer analyte;

after exposing the test portion to the decontamination process, contacting the test portion with a reagent for detecting the tracer analyte;

comparing the second quantity to a plurality of predetermined threshold quantities;

wherein a second quantity less than or equal to a first threshold quantity indicates the decontamination process was efficacious.

Embodiment VV is the method of Embodiment TT or Embodiment UU, wherein the dried composition further comprises a sugar.

Embodiment WW is a monitoring device, comprising:

a container comprising a first end with an opening dimensioned to receive a test element;

a test element disposed in the container, the test element comprising a test portion;

a dried composition releasably adhered to the test portion, the dried composition comprising a cellulose polymer and a predetermined quantity of a tracer analyte; and a reagent for detecting the tracer analyte, the reagent disposed in the container.

Embodiment XX is the monitoring device of Embodiment WW, wherein the dried composition further comprises a sugar.

Embodiment YY is a substantially dry composition comprising a cellulose polymer and a tracer analyte; wherein the composition has a dry mass; wherein the tracer analyte comprises a predetermined percentage of the mass of the composition.

Embodiment ZZ is the dry composition of Embodiment YY, wherein the dried composition further comprises a sugar.

Advantages and embodiments of this disclosure are further illustrated by the following examples, but the particular materials and amounts thereof recited in these examples, as well as other conditions and details, should not be construed to unduly limit this disclosure. All materials are commercially available or known to those skilled in the art unless otherwise stated or apparent.

EXAMPLES

Unless stated otherwise, all reagents used in the following examples were reagent-grade. 3M CLEAN-TRACE Water Test (Total ATP) test units and the 3M CLEAN-TRACE NGi Luminometer were obtained from 3M Company (St. Paul, Minn.).

Preparative Example 1

Stock Solutions of Ingredients used to Prepare Artificial Test Soil Compositions With the exception of butter, all of the solutions in Table 2 were prepared in deionized water.

TABLE 2

Stock Solutions of the following ingredients were prepared.

| Test Soil Ingredient | Source |
| --- | --- |
| Carboxymethyl cellulose (CMC) | Sigma, St. Louis, MO |
| Sucrose | Essential Everyday Brand, Cub Foods, Spokane, WA |

TABLE 2-continued

Stock Solutions of the following ingredients were prepared.

| Test Soil Ingredient | Source |
| --- | --- |
| Hemoglobin | Spectrum, New Brunswick, NJ |
| Bovine Albumin Serum (BSA) | Spectrum, New Brunswick, NJ |
| Butter | Daily Chef Brand, Bentonville, AR |
| FD&C Red Dye # 40 | Spectrum, New Brunswick, NJ |
| Adenosine Triphosphate (ATP) | Sigma, St. Louis, MO |

Examples 1-15

Formulation of Artificial Test Soil Compositions and Production of Tests Elements with Compositions Coated Thereon Appropriate volume aliquots of concentrated stock solutions of the ingredients shown in Table 2 were combined with deionized water to prepare the formulations of artificial test soil shown in Table 3.

TABLE 3

Example 1—Artificial Test Soil Ingredients for Examples 1-15. All values are reported in milligrams/mL. The butter was melted before it was added to each mixture.

| Example | CMC | Sugar | Albumin | Hemoglobin | Butter (Lipid) | Red Dye #40 | ATP |
| --- | --- | --- | --- | --- | --- | --- | --- |
| 1 | 7.1 | 284 | 8.6 | 0.83 | 0.27 | 0.14 | 0.009 |
| 2 | 8.5 | 227 | 8.6 | 0.83 | 0.27 | 0.14 | 0.009 |
| 3 | 10.6 | 142 | 8.6 | 0.83 | 0.27 | 0.14 | 0.009 |
| 4 | 14.1 | 0 | 8.6 | 0.83 | 0.27 | 0.14 | 0.009 |
| 5 | 4.7 | 189 | 8.6 | 0.83 | 0.27 | 0.14 | 0.009 |
| 6 | 5.6 | 151 | 8.6 | 0.83 | 0.27 | 0.14 | 0.009 |
| 7 | 7.1 | 95 | 8.6 | 0.83 | 0.27 | 0.14 | 0.009 |
| 8 | 9.4 | 0 | 8.6 | 0.83 | 0.27 | 0.14 | 0.009 |
| 9 | 4.7 | 284 | 8.6 | 0.83 | 0.27 | 0.14 | 0.009 |
| 10 | 5.6 | 227 | 8.6 | 0.83 | 0.27 | 0.14 | 0.009 |
| 11 | 7.1 | 142 | 8.6 | 0.83 | 0.27 | 0.14 | 0.009 |
| 12 | 7.1 | 189 | 8.6 | 0.83 | 0.27 | 0.14 | 0.009 |
| 13 | 8.5 | 151 | 8.6 | 0.83 | 0.27 | 0.14 | 0.009 |
| 14 | 10.6 | 95 | 8.6 | 0.83 | 0.27 | 0.14 | 0.009 |
| 15 | 2.35 | 94.7 | 8.6 | 0.83 | 0.27 | 0.14 | 0.009 |

Before being coated with one of the artificial test soil (ATS) formulations of Examples 1-15, the 3M CLEAN-TRACE Water Test (Total ATP) test unit swabs (hereinafter, "test elements") were cleaned by running them through an automated decontamination process (i.e., the long wash cycle (P06)) of a GETINGE 46-4 model washer disinfector (Getinge USA, Inc., Rochester, N.Y.) to ensure they were completely clean.

Manual Coating Process: To apply the ATS composition to the test element, the test portion of the test element was submerged into one of the artificial test soil liquid mixtures shown in Table 3. Unless specified otherwise, all experiments were done using test elements having the test portion 44a shown in FIGS. 2A-2B. An acid brush was used to uniformly distribute the coating and eliminate air bubbles. A clean KIMWIPE (Kimberly Clark) was used to wipe away any excess coating that was dripping off the test element. The coated test element samples were allowed to dry for 30 minutes in a 60° C. oven. Once dry, another coat of the same formulation was added by using an acid brush dipped in the soil to spread more of the soil over the end of the test element. This was repeated until the dipper had 4 coats of the same soil and all 4 coated had been dried. After application of the fourth coat the test element was dried for one hour.

Semi Automated Coating Process: Up to 70 prewashed dippers are mounted on the holder of a KSV DC 100 model dipper-coater (KSV Instruments; Helsinki, Finland). The swabs were dipped in the soil using a process controlled by the KSV software supplied with the instrument. The dipping down speed was set to 20 millimeter/minute. After 90 seconds of contact, the dippers were withdrawn at a speed of 10 millimeter/minute to avoid air bubble formation. The coated samples were allowed to dry for 30 minutes in a 60° C. oven. The coating process was repeated 4 times. The fourth coat was dried for one hour.

In order to approximate the weight percent of each ingredient of the dried ATS compositions of Examples 1-15, a measured weight of one of the formulations was placed into a beaker and then dried in an oven. Additionally, the estimated dry weight concentration of each ingredient is calculated in Table 4 below.

TABLE 4

Approximate weight percent of each ingredient of the dried ATS compositions of Examples 1-15

| Example | CMC | Sugar | Albumin | Hemoglobin | Butter (Lipid) | Red Dye #40 | ATP |
|---|---|---|---|---|---|---|---|
| 1 | 2.36 | 94.37 | 2.86 | 0.28 | 0.09 | 0.05 | 0.003 |
| 2 | 3.46 | 92.52 | 3.51 | 0.34 | 0.11 | 0.06 | 0.004 |
| 3 | 6.53 | 87.42 | 5.29 | 0.51 | 0.17 | 0.09 | 0.006 |
| 4 | 58.90 | 0.00 | 35.92 | 3.47 | 1.13 | 0.58 | 0.038 |
| 5 | 2.31 | 92.86 | 4.23 | 0.41 | 0.13 | 0.07 | 0.004 |
| 6 | 3.36 | 90.72 | 5.17 | 0.50 | 0.16 | 0.08 | 0.005 |
| 7 | 6.34 | 84.87 | 7.68 | 0.74 | 0.24 | 0.13 | 0.008 |
| 8 | 48.86 | 0.00 | 44.70 | 4.31 | 1.40 | 0.73 | 0.047 |
| 9 | 1.57 | 95.13 | 2.88 | 0.28 | 0.09 | 0.05 | 0.003 |
| 10 | 2.31 | 93.63 | 3.55 | 0.34 | 0.11 | 0.06 | 0.004 |
| 11 | 4.47 | 89.34 | 5.41 | 0.52 | 0.17 | 0.09 | 0.006 |
| 12 | 3.45 | 91.77 | 4.18 | 0.40 | 0.13 | 0.07 | 0.004 |
| 13 | 5.02 | 89.17 | 5.08 | 0.49 | 0.16 | 0.08 | 0.005 |
| 14 | 9.18 | 82.29 | 7.45 | 0.72 | 0.23 | 0.12 | 0.008 |
| 15 | 2.20 | 88.59 | 8.04 | 0.78 | 0.25 | 0.13 | 0.008 |
| MIN* | 1.57 | 0.00 | 2.86 | 0.28 | 0.09 | 0.05 | 0.0030 |
| MAX* | 58.9 | 95.13 | 44.7 | 4.31 | 1.40 | 0.73 | 0.047 |

*Minimum and Maximum.

The prepared test elements with dried ATS formulations were evaluated using an industrial hospital instrument washer disinfector, a GETINGE 46-4 model washer disinfector. Four different automated decontamination processes were programmed to test the ability of the test elements to indicate the effectiveness of the washer disinfector decontamination process. Decontamination Test Process 1 was programmed to include a wash step that is generally considered adequate and a rinse step that is also generally considered adequate. Decontamination Test Process 2 was programmed to include a wash step that is generally considered adequate and a rinse step that is generally considered faulty (i.e., no rinse steps were included). Decontamination Test Process 3 was programmed to include a wash step that is generally considered faulty (i.e., inadequate amount of detergent and inadequate length of washing time) and a rinse step that is generally considered adequate. Decontamination Test Process 4 was programmed to include a wash step that is generally considered faulty (i.e., inadequate amount of detergent and inadequate length of washing time) and a rinse step that is also generally considered faulty (i.e., no rinse steps were included). The parameters for each decontamination test process are shown in Table 5.

TABLE 5

Decontamination Test Processes 1-4

| | Test Process 1 Adequate Wash Adequate Rinse | Test Process 2 Adequate Wash Faulty Rinse | Test Process 3 Faulty Wash Adequate Rinse | Test Process 4 Faulty Wash Faulty Rinse |
|---|---|---|---|---|
| Wash Step Parameters | | | | |
| Wash #1 Temp ° C. | 48.9 | 48.9 | 46.1 | 46.1 |
| Wash #1 Detergent Dose mL | 40 | 40 | 10 | 10 |
| Wash #1 Time min:sec | 3:00 | 3:00 | 0:05 | 0:05 |
| Wash #2 Temp ° C. | 54.4 | 54.4 | 48.9 | 48.9 |
| Wash #2 Detergent Dose mL | 40 | 40 | 10 | 10 |
| Wash #2 Time min:sec | 3:00 | 3:00 | 0:05 | 0:05 |
| Rinse Step parameters | | | | |
| Rinse #1 Fill Type | Hot | Cold | Hot | Cold |
| Rinse #1 Time min:sec | 1:00 | 0:00 | 1:00 | 0:00 |
| Rinse #2 Fill Type | Hot | None | Hot | None |
| Rinse #2 Time min:sec | 1:00 | None | 1:00 | None |
| Final Rinse Dose Temp ° C. | 70 | 20 | 70 | 20 |
| Final Rinse Max Temp ° C. | 90 | 40 | 90 | 40 |

TABLE 5-continued

Decontamination Test Processes 1-4

| | Test Process 1 Adequate Wash Adequate Rinse | Test Process 2 Adequate Wash Faulty Rinse | Test Process 3 Faulty Wash Adequate Rinse | Test Process 4 Faulty Wash Faulty Rinse |
|---|---|---|---|---|
| Final Rinse Time min:sec | 1:00 | 0:00 | 1:00 | 0:00 |

Additionally, all decontamination test processes were performed using GETINGE 46-4 model washer disinfector and used the manufacturer recommended detergents and lubricants during the processes. Table 6 shows the order in which the detergents and lubricant are used. The enzymatic detergent is used in the wash #1 step, whereas alkaline detergent is used in wash #2 step. The lubricant is used and the final rinse step.

TABLE 6

Types of detergents and lubricants and the dispensing order

| Type of detergent | Renuzyme Plus (Enzyme) | Alkaline Detergent | Instrument Lubricant Plus |
|---|---|---|---|
| Order of dispensing in the Washer | First | Second | Third |
| Volume dispense | 40 ml | 40 ml | 8 ml |

Test elements were prepared as described above and duplicate test elements of each configuration were placed inside the washer disinfector and exposed to one of the Decontamination Test Processes 1-4. After processing the test elements in the decontamination test processes, the test elements were removed from the washer, returned to their respective ATP test units, and the amount of ATP on each monitoring device test element was measured in a bioluminescent (i.e., luciferin/luciferase reaction) assay using a 3M CLEAN-TRACE NG Luminometer.

TABLE 7

Average amount of ATP detected from duplicate coated test elements after Decontamination Test Processes 1-4 for artificial test soil ATS formulations (Examples 1-15). All results are reported in Log10 Average Relative Light Units (RLU) measured by the luminometer. The Controls were test elements that were not exposed to any decontamination process.

| Example | Test Process 1 | Test Process 2 | Test Process 3 | Test Process 4 | Control |
|---|---|---|---|---|---|
| 1 | 2.106 | 3.021 | 2.917 | 5.773 | 5.999 |
| 2 | 2.129 | 4.959 | 2.918 | 5.984 | 6.002 |
| 3 | 2.221 | 3.888 | 2.949 | 6.027 | 6.043 |
| 4 | 2.152 | 2.597 | 2.953 | 5.964 | 6.026 |
| 5 | 2.305 | 2.953 | 3.003 | 5.930 | 6.070 |
| 6 | 2.381 | 2.811 | 2.971 | 5.986 | 6.070 |
| 7 | 2.296 | 2.907 | 2.970 | 5.897 | 6.085 |
| 8 | 2.059 | 2.635 | 2.956 | 5.697 | 6.012 |
| 9 | 2.035 | 2.950 | 2.859 | 5.619 | 6.034 |
| 10 | 1.908 | 3.084 | 2.968 | 5.798 | 6.040 |
| 11 | 2.166 | 2.812 | 2.962 | 5.974 | 6.058 |
| 12 | 2.329 | 2.965 | 3.017 | 6.024 | 6.030 |
| 13 | 2.238 | 4.377 | 2.928 | 6.036 | 6.056 |
| 14 | 2.249 | 3.842 | 2.927 | 6.035 | 6.072 |
| 15 | 1.200 | 1.410 | 1.150 | 1.900 | 6.018 |

Comparative Example 1

Comparison of Artificial Test Soil Composition having Polyvinyl Alcohol to Artificial Test Soil Composition having a Cellulose Polymer A comparative ATS example, which did not include a cellulose polymer in the composition, was prepared First a stock solution (1mg/mL) of ATP was prepared in sterile deionized water. This stock solution was serially diluted in sterile deionized water to produce one working solution containing 0.7 microgram/mL ATP. An aliquot of this ATP working solution was added to individual mixing jars. A solution of FD&C Red Dye # 40 was prepared by dissolving 160 mg of F&DC Red Dye #40 into 40 mL of sterile water. The 4 mg/mL Red Dye #40 solution was added to each of the mixing jars containing the ATP working solution and the mixing jars were placed in a water bath at 80° C. Polyvinyl alcohol (PVA) CELVOL 443, obtained from Sekisui Specialty Chemicals (Secaucus, N.J.), was added to the jar at a rate of about 1.0 gram/minute with stirring to obtain a final concentration of CELVOL 443 PVA of 9.7 wt. %. Each mixture was stirred for about one hour to allow the PVA to fully dissolve. The final concentration of ATP was 1 microgram/mL. The final concentration of Red Dye #40 was 0.13 mg/mL. The Red Dye was added primarily for visibility when coating the test elements. Test portions of individual test elements from (3M CLEAN-TRACE Water Test (Total ATP)) were coated using the manual coating process with the artificial test soil of Comparative Example 2, in the same coating manner as described above. Replicate Comparative Example 2 test elements, as well as test elements prepared according to Example 3 and Example 15 (above), were exposed to Decontamination Test Processes 1-4 as described above. The test elements coated with the compositions of Examples 3 and 15 were coated using the automated coating process. After processing the test elements in the washer-disinfector, the amount of ATP remaining on each test portion was evaluated using a 3M CLEAN-TRACE NG Luminometer and the results, reported in RLUs, and are shown in Table 8. The data indicate that, after exposure to an adequate decontamination process (Test Process 1), less ATP was detectable on both Examples 3 and 15 test elements than was detectable on Comparative Example 1 test elements. In addition, after exposure to a faulty decontamination process (Test Processes 2-4), more ATP was detectable on both Examples 3 and 15 test elements than was detectable on Comparative Example 2 test elements.

TABLE 8

Amount of residual ATP detected from coated test elements after exposure to Decontamination Test Processes 1-4. All results are reported in $LOG_{10}$ Average Relative Light Units (RLU).

| Decontamination Test Process | Example 3 (n = 15) | Example 15 (n = 6) | Comparative Example 1 (n = 15) |
|---|---|---|---|
| 1 | 2.69 ± 0.07 | 1.16 ± 0.09 | 3.04 ± 0.07 |
| 2 | 6.07 ± 0.05 | 1.41 ± 0.06 | 4.98 ± 0.17 |
| 3 | 4.12 ± 0.07 | 1.15 ± 0.04 | 3.07 ± 0.7 |
| 4 | 6.12 ± 0.01 | 1.92 ± 0.14 | 4.89 ± 0.08 |
| Control | 6.12 ± 0.03 | 6.26 ± 0.01 | 5.98 ± 0.02 |

Examples 16-20

Effect of ATP Quantity on the Detection of Faulty Decontamination Processes

Artificial Test Soil compositions were prepared and coated onto test elements to evaluate the effect of different levels of ATP in the artificial test soil on the detection of faulty decontamination processes. Six aliquots of the artificial test soil were prepared according to the formulation described in Example 3 were prepared identically with the exception that the amount of ATP was varied (the concentration of ATP in the liquid composition used to coat the test elements is shown in Table 9) to create the compositions of Examples 16-20. Replicate test elements from Examples 3 and 16-20 were exposed to Decontamination Test Processes 1-4 as described above. After exposure to the decontamination test processes, the residual ATP on each test element was quantified using a luminometer as described above. The results, reported in RLUs, are shown in Table 9.

TABLE 9

Amount of ATP detected from coated test elements after Decontamination Test Processes 1-4. All results are reported in $LOG_{10}$ Average Relative Light Units (RLU)

|  | Cycle Efficacy | Decontamination Test Process | $LOG_{10}$ RLU (n = 6) |
|---|---|---|---|
| Example 3 | Adequate | 1 | 2.95 ± 0.43 |
| (3 µg/ml ATP) | Faulty | 2 | 3.67 ± 0.36 |
|  |  | 3 | 4.13 ± 0.05 |
|  |  | 4 | 5.94 ± 0.07 |
| Example 16 | Adequate | 1 | 2.69 ± 0.07 |
| (9 µg/ml ATP) | Faulty | 2 | 6.07 ± 0.05 |
|  |  | 3 | 4.12 ± 0.07 |
|  |  | 4 | 6.12 ± 0.01 |
| Example 17 | Adequate | 1 | 2.84 ± 0.17 |
| (18 µg/ml ATP) | Faulty | 2 | 4.28 ± 0.40 |
|  |  | 3 | 4.14 ± 0.08 |
|  |  | 4 | 6.07 ± 0.02 |
| Example 18 | Adequate | 1 | 2.57 ± 0.10 |
| (27 µg/ml ATP) | Faulty | 2 | 3.57 ± 0.15 |
|  |  | 3 | 4.16 ± 0.09 |
|  |  | 4 | 6.09 ± 0.01 |
| Example 19 | Adequate | 1 | 2.81 ± 0.43 |
| (36 µg/ml ATP) | Faulty | 2 | 3.77 ± 0.16 |
|  |  | 3 | 4.12 ± 0.08 |
|  |  | 4 | 6.09 ± 0.01 |
| Example 20 | Adequate | 1 | 2.77 ± 0.11 |
| (45 µg/ml ATP) | Faulty | 2 | 3.73 ± 0.09 |
|  |  | 3 | 4.15 ± 0.08 |
|  |  | 4 | 6.09 ± 0.01 |

Examples 21-25

Effect of the 3-dimensional Shape of the Test Portion of Test Elements

Five separate groups of test elements were constructed. Each group of test elements had a test portion having one of five different topological features (shapes), as shown in the figures and described above. The test portions of Example 21-24 test elements were coated with the artificial test soil composition of Example 3 using the manual coating process. The test portions of Example 25 test elements were coated with the artificial test soil composition of Example 3 using the semi-automated coating process. After drying the coated composition, representative test elements from Examples 21-24 were placed in a Getinge 46 washer and were washed using Decontamination Test Process 1 or Decontamination Test Process 3, as specified in Table 10. After completion of the decontamination test processes, the amount of test soil ATP remaining on each test element was measured with a luminometer as described above and the results are presented in Tables 10 and 11. The data in Table 10 indicate that each of the differently-shaped test portions retained different amounts of residual ATP for each of the two cycles. Regardless of the shape of the test elements, the $LOG_{10}$ RLU measured from ATP retained on test elements exposed to Decontamination Test Process 3 were all higher than the $LOG_{10}$ RLU measured from ATP retained on test elements exposed to Decontamination Test Process 1. This indicates that test portions having any of the variety of shapes that were tested were able to distinguish between Decontamination Test Processes 1 and 3.

TABLE 10

Amount of ATP detected from coated test elements of Different Shapes after Decontamination Test Processes 1 and 3. All results are reported as the average $LOG_{10}$ Relative Light Units (RLU) measured from duplicate test elements.

| Test Portion Design | Test Process 1 $LOG_{10}$ RLU | Test Process 3 $LOG_{10}$ RLU | Ratio $LOG_{10}$ RLU (Test Process 3)/ $LOG_{10}$ RLU (Test Process 1) |
|---|---|---|---|
| Example 21 (Shape 1, FIGS. 2A-2B) | 1.67 | 2.19 | 1.31 |
| Example 22 (Shape 2, FIGS. 5A-5B) | 3.26 | 3.61 | 1.11 |
| Example 23 (Shape 3, FIGS. 3A-3B) | 3.01 | 3.63 | 1.21 |
| Example 24 (Shape 4, FIGS. 4A-4B) | 2.96 | 3.57 | 1.21 |

The test elements of Example 25 ("Shape 5") had a test portion that was substantially planar (i.e., the test portion did not comprise a cavity in the coated surface). These test elements were formed by removing (with a razor blade) the ridges between the cavities in the test portion illustrated in FIG. 2A to form the test portion illustrated in FIG. 6, i.e., a simple, cylindrically-shaped test portion. The Example 25 test elements were placed in a Getinge 46 washer and were exposed to one of Decontamination Test Processes 1-4 (described above), as specified in Table 11. After exposing the test elements to the decontamination processes, the residual ATP on each of the test elements was measured with a luminometer as described above. The data in Table 11 indicate that each of the differently-shaped test portions retained different amounts of residual ATP for each of the two cycles.

TABLE 11

Amount of residual ATP detected from Example 25 test elements after exposure to Decontamination Test Processes 1-4. All results are reported as the average $LOG_{10}$ Relative Light Units (RLU) measured from 28 test elements per cycle.

| Process Adequacy | Decontamination Test Process | $LOG_{10}$ RLU |
|---|---|---|
| Adequate | 1 | 2.20 ± 0.29 |
| Faulty | 2 | 2.18 ± 0.27 |
|  | 3 | 2.17 ± 0.12 |
|  | 4 | 2.62 ± 0.20 |

Examples 26-28 and Comparative Example 2

The following stock solutions were prepared in deionized water: Carboxymethylcellulose (1.5 g/100 mL), Sucrose (70 g/100 mL), Hemoglobin (2.7 g/100 mL), Bovine Serum Albumin (30 g/100 mL), FD&C Red Dye #40 (0.4 g/100 mL), and ATP (0.1 g/100 mL). Using the composition of Example 3 as the starting point, the compositions of Examples 26-28 and Comparative Example 2 were prepared, each of them lacking one of the components (e.g., CMC, sucrose, BSA, or Hemoglobin) present in the composition of Example 3, as shown in Table 12. Each of the compositions of Examples 26-29 was deposited onto the test portion of test elements using the semi-automated coating process described above. Replicate test elements (15 test elements per process) were exposed to the Decontamination Test Processes 1-4 described above. After exposing the test elements to the decontamination test processes, the residual ATP on each test portion was measured with a luminometer as described above. The results are shown in Table 13.

TABLE 12

The volume (in milliliters) of each respective stock solution that was used to make the compositions of Examples 26-29 is reported in this table.

| Component | Comparative Example 2 | Example 26 | Example 27 | Example 28 |
|---|---|---|---|---|
| CMC Stock | 0.0 | 141.7 | 141.7 | 141.7 |
| Sucrose Stock | 40.7 | 0.0 | 40.7 | 40.7 |
| BSA Stock | 5.7 | 5.7 | 0.0 | 5.7 |
| Hemoglobin Stock | 6.4 | 6.4 | 6.4 | 0.0 |
| Butter | 0.1 | 0.1 | 0.1 | 0.1 |
| FD&C Red Dye # 40 Stock | 5.7 | 5.7 | 5.7 | 5.7 |
| ATP Stock | 1.8 | 1.8 | 1.8 | 1.8 |
| Di water | 141.7 | 40.7 | 5.7 | 6.4 |
| Total volume (ml) | 202.0 | 202.0 | 202.0 | 202.0 |

TABLE 13

Residual ATP remaining on test portions of Comparative Example 2 and Examples 26-28 after exposure to Decontamination Test Processes 1-4. All results are reported in $LOG_{10}$ Average Relative Light Units (RLU). N = 15 for each condition.

| | Comparative Example 2 | Example 26 | Example 27 | Example 28 |
|---|---|---|---|---|
| Test Process 1 | 1.69 ± 0.23 | 1.96 ± 0.16 | 2.03 ± 0.14 | 1.91 ± 0.24 |
| Test Process 2 | 2.21 ± 0.19 | 2.69 ± 0.26 | 2.62 ± 0.14 | 2.91 ± 0.22 |
| Test Process 3 | 1.73 ± 0.24 | 2.27 ± 0.17 | 2.39 ± 0.10 | 2.26 ± 0.19 |
| Test Process 4 | 2.82 ± 0.31 | 3.13 ± 0.29 | 4.08 ± 0.18 | 5.45 ± 0.32 |

The complete disclosure of all patents, patent applications, and publications, and electronically available material cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

Various modifications may be made without departing from the spirit and scope of the invention. These and other embodiments are within the scope of the following claims.

The invention claimed is:

1. A monitoring device, comprising:
   a container comprising a first end with an opening dimensioned to receive a test element;
   the test element disposed in the container, the test element comprising a test portion;
   a dried composition releasably adhered to the test portion, the dried composition comprising a cellulose polymer, sugar, and a predetermined quantity of an adenine nucleotide, wherein the sugar and the cellulose polymer are present in the composition at a sugar:cellulose polymer mass ratio of about 9:1 to about 60:1, inclusive; and
   a reagent for detecting the adenine nucleotide, the reagent disposed in the container.

2. The monitoring device of claim 1, wherein the cellulose polymer comprises a water-soluble cellulose derivative.

3. The monitoring device of claim 1, further comprising a secural element.

4. A kit, comprising the monitoring device of claim 1.

5. The kit of claim 4, further comprising a means to secure the test element.

6. The kit of claim 4, further comprising an article comprising a receiver dimensioned to receive the test element and to restrict fluidic accessibility to the test portion.

7. A system, comprising:
   a monitoring device, comprising:
     a container comprising a first end with an opening dimensioned to receive a test element;
     the test element disposed in the container, the test element comprising a test portion;
     a dried composition releasably adhered to the test portion, the dried composition comprising a cellulose polymer, sugar, and a predetermined quantity of an adenine nucleotide, wherein the sugar and the cellulose polymer are present in the composition at a sugar:cellulose polymer mass ratio of about 9:1 to about 60:1, inclusive;
     a reagent for detecting the adenine nucleotide, the reagent disposed in the container;
   an analytical instrument for detecting a reaction between the adenine nucleotide and the reagent; and
   a processor configured to receive electronic data from the analytical instrument.

8. A method of assessing the efficacy of a decontamination process, comprising:
   exposing a test portion of a monitoring device to a decontamination process;
     wherein the test portion includes a dried composition removably adhered thereto;
     wherein the dried composition comprises a cellulose polymer, a sugar, and
   a predetermined first quantity of an adenine nucleotide, wherein the sugar and the cellulose polymer are present in the composition at a sugar:cellulose polymer mass ratio of about 9:1 to about 60:1, inclusive;
   after exposing the test portion to the decontamination process, contacting the test portion with a reagent for detecting the adenine nucleotide;

using the detection reagent to measure a second quantity of the adenine nucleotide remaining on the test portion; and comparing the second quantity to a predetermined first threshold quantity.

9. The method of claim 8, wherein comparing the second quantity to a predetermined threshold quantity further comprises comparing the second quantity to a plurality of predetermined threshold quantities.

10. The method of claim 9, further comprising the steps of comparing the second quantity of adenine nucleotide to a second threshold quantity and reporting an outcome of an assessment of the efficacy:

wherein, when the second quantity is less than or equal to the first threshold quantity, the outcome of the decontamination process is reported to indicate the process was efficacious;

wherein, when the second quantity is greater than the first threshold quantity but less than or equal to a second threshold quantity, the outcome of the decontamination process is reported to indicate the process had a deficiency associated with a first predetermined parameter of the decontamination process.

11. The method of claim 8, further comprising the step of placing the test portion of the monitoring device into a receiver configured to restrict fluidic accessibility to the test portion.

* * * * *

UNITED STATES PATENT AND TRADEMARK OFFICE
CERTIFICATE OF CORRECTION

| | | |
|---|---|---|
| PATENT NO. | : 10,287,618 B2 | Page 1 of 1 |
| APPLICATION NO. | : 15/129442 | |
| DATED | : May 14, 2019 | |
| INVENTOR(S) | : Francois Ahimou | |

It is certified that error appears in the above-identified patent and that said Letters Patent is hereby corrected as shown below:

On the Title Page

(72) Inventors:, Line 5, delete "Shangahi" and insert -- Shanghai --, therefor.

In the Specification

Column 4
Line 21, delete "FIG." and insert -- FIGS. --, therefor.

Column 8
Line 31, delete "and or" and insert -- and/or --, therefor.

Column 11
Line 8, delete "albumin)" and insert -- albumin). --, therefor.

Column 13
Line 26, delete "and or" and insert -- and/or --, therefor.
Line 27, delete "and or" and insert -- and/or --, therefor.

Column 19
Line 8-10 (approx.), delete "In any embodiment, the plurality of threshold quantities comprises a second threshold quantity and the second threshold quantity is about 1% of the first quantity." and insert the same on Column 19, Line 7, as a continuation of the same paragraph.

Signed and Sealed this
Third Day of September, 2019

Andrei Iancu
*Director of the United States Patent and Trademark Office*